United States Patent
Berlin et al.

(10) Patent No.: US 8,088,628 B2
(45) Date of Patent: Jan. 3, 2012

(54) STIMULATED AND COHERENT ANTI-STOKES RAMAN SPECTROSCOPIC METHODS FOR THE DETECTION OF MOLECULES

(75) Inventors: Andrew Arthur Berlin, San Jose, CA (US); Christopher Marc Gerth, Santa Clara, CA (US); Tae-Woong Koo, South San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 1402 days.

(21) Appl. No.: 10/262,349

(22) Filed: Sep. 30, 2002

(65) Prior Publication Data

US 2004/0063214 A1 Apr. 1, 2004

(51) Int. Cl.
*G01N 21/03* (2006.01)

(52) U.S. Cl. ............ 436/165; 436/164; 436/94; 372/92; 372/107

(58) Field of Classification Search .................. 436/164, 436/165; 356/300, 301, 337
See application file for complete search history.

(56) References Cited

U.S. PATENT DOCUMENTS

| | | | |
|---|---|---|---|
| 5,303,710 A | 4/1994 | Bashkansky et al. | |
| 5,306,403 A | 4/1994 | Vo-Dinh | |
| 5,452,084 A | 9/1995 | Mitchell et al. | 356/301 |
| 5,786,893 A | 7/1998 | Fink et al. | |
| 5,904,824 A | 5/1999 | Oh | |
| 6,002,471 A | 12/1999 | Quake | |
| 6,174,677 B1 | 1/2001 | Vo-Dinh | |
| 6,197,503 B1 | 3/2001 | Vo-Dinh et al. | |
| 6,208,680 B1 | 3/2001 | Chirovsky et al. | |
| 6,230,991 B1 | 5/2001 | Steinruck et al. | |
| 6,379,974 B1 | 4/2002 | Parce et al. | |
| 6,409,900 B1 | 6/2002 | Parce et al. | |
| 6,425,972 B1 | 7/2002 | McReynolds | |
| 6,514,767 B1 | 2/2003 | Natan | 436/166 |
| 2002/0024662 A1 | 2/2002 | Ueno et al. | |
| 2002/0064800 A1 | 5/2002 | Sando et al. | |
| 2007/0252983 A1* | 11/2007 | Tong et al. | 356/301 |

FOREIGN PATENT DOCUMENTS

| | | |
|---|---|---|
| EP | 0 618 442 A1 | 3/1994 |
| EP | 0 618 442 | 10/1994 |
| EP | 0 814 333 A2 | 6/1997 |
| EP | 0 814 333 | 12/1997 |
| WO | WO 99/44045 | 9/1999 |
| WO | WO 02/44412 A1 | 6/2002 |
| WO | 02/71013 A1 | 9/2002 |

(Continued)

OTHER PUBLICATIONS

Graham et al. "Selective detection of deoxyribonucleic acid at ultralow concentrations by SERRS", Anal. Chem., 1997, v. 69, pp. 4703-4707.*

(Continued)

*Primary Examiner* — Vickie Kim

(74) *Attorney, Agent, or Firm* — Pillsbury Winthrop Shaw Pittman LLP

(57) ABSTRACT

Spectroscopic analysis systems and methods for analyzing samples are disclosed which exploit inelastically scattering radiation to amplify optical signals from an irradiated sample. Samples are irradiated in a chamber having a resonant cavity containing a plurality of affixed reflectors, where selective Stokes scattered radiation is transmitted to a detector for determination of sample identity. Coupling the spectroscopic analysis system and method with a nucleic acid sequencing system is also disclosed for determining nucleic acid sequences.

11 Claims, 12 Drawing Sheets

FOREIGN PATENT DOCUMENTS

| WO | WO 03/027307 | 4/2003 |
|---|---|---|
| WO | WP 03/027307 | 4/2003 |
| WO | 2004/031749 A2 | 4/2004 |

OTHER PUBLICATIONS

Xie et al. "Optical studies of single molecules at room temperature", Annu. Rev. Phys. Chem., 1998, v. 49, pp. 441-480.*

Kneipp et al. "Ultrasensitive chemical analysis by Raman spectroscopy", Chem. Rev., 1999, v. 99, pp. 2957-2975.*

Castro et al. "Fluorescence detection and size measurement of single DNA molecules", Anal. Chem., 1993, v. 65, pp. 849-852.*

Otto et al. "Progress in instrumentation for Raman micro-spectroscopy and Raman imaging for cellular biophysics", The Interne Journal of Vibrational Spectroscpy, v. 2, edition 3, accepted Aug. 1998.*

Hill et al. "Fluorescence image of a single molecule in a microsphere: model", J. Opt. Soc., Am. B, Nov. 1999, vol. 16, No. 11, pp. 1868-1873.*

Hennrich et al. "Vacuum stimulated Raman scattering based on adiabatic passage in a high-finesse optical cavity", Phys. ,Rev. Lett., 2000, v. 85, No. 23, pp. 4872-4875.*

Cheng et al. "Laser-scanning coherent anti-Stokes Raman scattering microscopy and application to cell biology", Biophys. J., Jul. 2002, v. 83, pp. 502-509.*

Cheng et al. "Multiplex coherent anti-Stokes Raman scattering microspectroscopy and study of lipid vesicles", J. Phys. Chem. B., Aug. 29, 2002, v. 106, pp. 8493-8498.*

Martini et al. "Molecular Raman effect in the optical microcavity: QED vacuum confinement of an inelastic quantum scattering process", Phys. Rev. A, 1996, v. 53, No. 1, pp. 471-480.*

Vahala "Optical microcavities", Nature, 2003, v. 242, pp. 839-846.*

Norris et al. "Probing Single Molecules with Whispering Gallery Modes of Microspheres" http://www.stanford.edu/group/moerner/pumping.html, Jan. 2003, 1-3.*

Ishikawa et al. "Single-Molecule Imaging and Spectroscopy Using Fluorescence and Surface-Enhanced Raman Scattering", J. Biol. Phys., 2002, v. 28, pp. 573-585.*

Lutfullah Maleki et al. National Aeronautics and Space Administration Contract No. NAS 7-918, Enhanced Optical Microresonators for Detecting Molecules. Nov. 11, 2001 NASA Tech Brief vol. 25, No. 11 from JPL New Technology Report NPO-21239. pp. 1-4.

Enhanced Optical Microresonators for Detecting Molecules; Sensitivity and Selectivity would be enhanced by use of Fluorophores. [Online] Retrieved Jun. 20, 2002 Retrieved from the Internet http://www.nasatech.com/Briefs/Nov01/Npo21239.html. pp. 1-3.

Doering, et al., "Spectroscopic Tags Using Dye-Embedded Nanoparticles and Surface—Enhanced Raman Scattering", *Analytical Chemistry*, :5-9.

Mulvaney, et al., "Glass-Coated, Analyte-Tagged Nanoparticles: A New Tagging System Based on *Detection* with Surface-Enhanced Raman Scattering", *Am Chem Soc.* 19:4784-4790 (2003).

European Patent Office Communication corresponding to EP Application No. 03 774 515.5, dated Dec. 23, 2010.

* cited by examiner

STIMULATED AND COHERENT ANTI-STOKES RAMAN SPECTROSCOPIC METHODS FOR THE DETECTION OF MOLECULES

BACKGROUND

Field

Embodiments of the invention relate to analyzing a sample with Raman spectroscopy. In particular, embodiments relate to analyzing a sample containing a single nucleic acid derivative of interest contained within a spectroscopic analysis chamber with stimulated or coherent anti-Stokes Raman spectroscopy.

BACKGROUND INFORMATION

Deoxyribonucleic acid (DNA) sequencing has many commercially important applications in the fields of medical diagnosis, drug discovery, and treatment of disease. Existing methods for DNA sequencing, based on detection of fluorescence labeled DNA molecules that have been separated by size, are limited by the length of the DNA that can be sequenced. Typically, only 500 to 1,000 bases of DNA sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming. It also typically requires the use of fluorescent or radioactive labels, which can potentially pose safety and waste disposal problems.

More recently, methods for DNA sequencing have been developed involving hybridization to short oligonucleotides of defined sequence, attached to specific locations on DNA chips. Such methods may be used to infer short DNA sequences or to detect the presence of a specific DNA molecule in a sample, but are not suited for identifying long DNA sequences.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

Described herein are spectroscopic analysis systems and methods for analyzing samples with Raman spectroscopy. In the following description, numerous specific details are set forth. However, it is understood that embodiments of the invention may be practiced without these specific details. For example, a practitioner may use a spectroscopic analysis chamber other than the specific chambers disclosed herein. As another example, a practitioner may use another spectroscopy technique than the specific stimulated and coherent anti-Stokes Raman spectroscopies disclosed herein. In other instances, well-known structures and techniques have not been shown in detail in order to avoid obscuring the understanding of this description. It is recognized that there is a generally high level of skill in the arts of spectroscopy and in fabricating chambers as disclosed herein.

Embodiments of the invention may be used in conjunction with DNA sequencing. One exemplary method for DNA sequencing may involve the ordered deconstruction of a DNA molecule into smaller nucleotide components, for example through the use of enzymes, and then analyzing and identifying the nucleotides to determine the ordered sequence of the nucleotides in the original DNA molecule. Spontaneous Raman spectroscopy has been attempted for identification of nucleotides. During spontaneous Raman spectroscopy, the sample containing the nucleotide is exposed to radiation, and a small portion of the radiation that interacts with the nucleotide is scattered due to the spontaneous Raman scattering effect according to vibrational characteristics of the nucleotide.

Unfortunately, in spontaneous Raman spectroscopy, the optical signals scattered from nucleotides in dilute solution are generally very weak, and the resulting generally low probability of detecting the optical signals makes the approach insensitive, inaccurate, and unreliable. There have been efforts to improve the accuracy of this approach by making multiple measurements and performing data averaging, although this takes more time, and may not be desirable in a rapid DNA sequencing environment. There have also been efforts to improve the strength of the optical signal by attaching chemical moieties, such as fluorescent chromophores, to the nucleotides in order to enhance their luminescent or fluorescent properties. Reliably and consistently attaching these moieties remains problematic. The moieties or their buffer solutions may be unstable. In some instances, the moieties fail to attach altogether. In other instances the moieties that do attach have different characteristics and cause their nucleotides to have a different spectroscopic response. Such problems make it difficult to accurately and reliably identify the nucleotides. In addition, the processes to attach the chemical moieties add additional time and complexity to the analysis. These problems may be overcome by the methods and systems disclosed herein.

Figure 1:
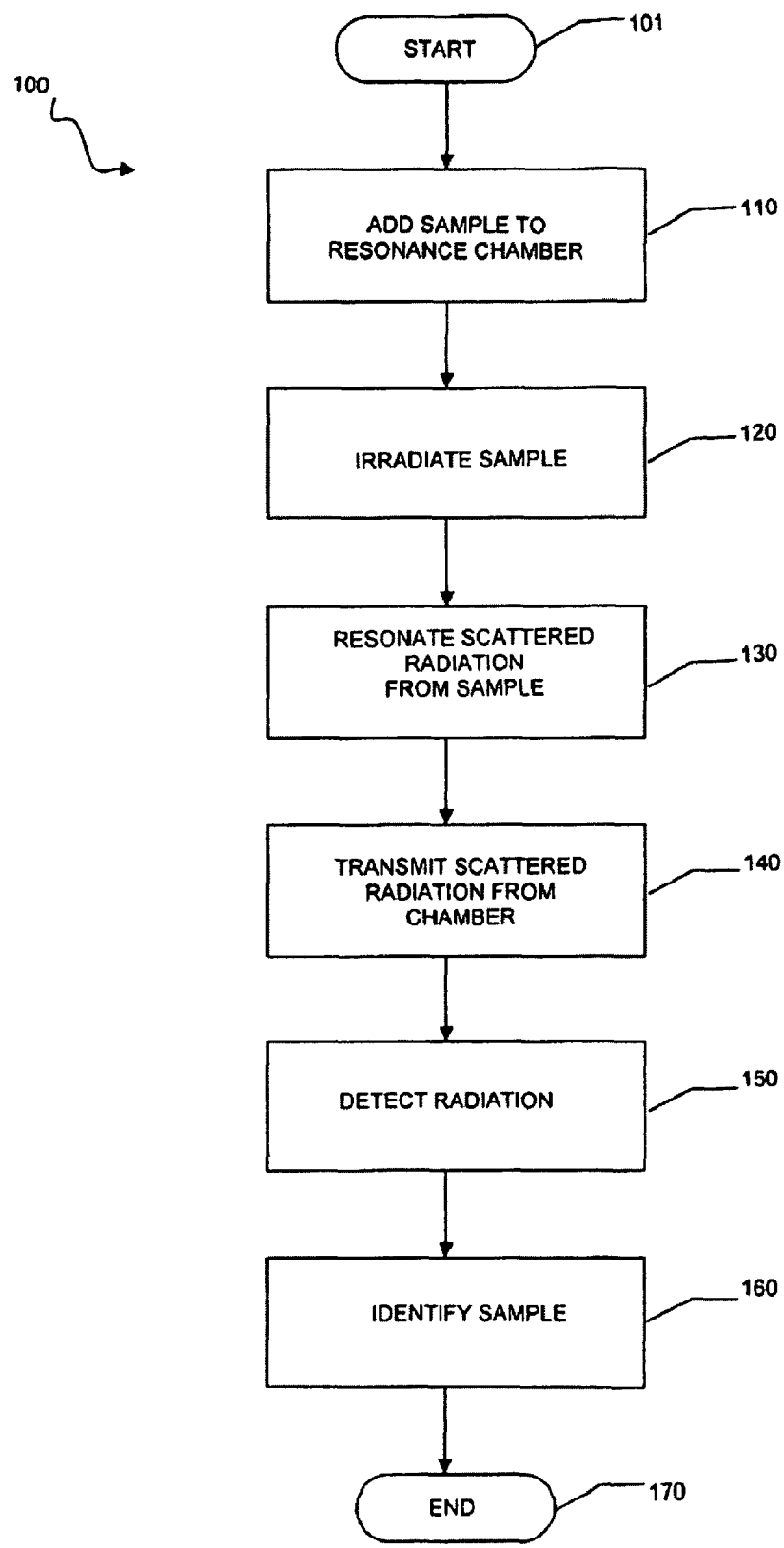
FIG. 1 shows a method for identifying a sample based on a resonance enhanced spectroscopic analysis, according to embodiments of the invention.

FIG. 1 shows a method for identifying a sample based on a resonance enhanced stimulated Raman spectroscopic analysis, according to embodiments of the invention. The method allows identifying a sample based on spectroscopic data that serves as a fingerprint or signature for the sample. In brief, the method includes adding a sample, such as a single molecule of interest in solution, to a resonant spectroscopic analysis chamber at block 110, analyzing the sample with a resonance enhanced stimulated Raman spectroscopy at blocks 120-150, and identifying the sample based on the analysis at block 160. In some embodiments of the invention, the resonance enhanced stimulated Raman spectroscopy may include irradiating a sample contained in a resonance chamber at block 120, allowing the scattering radiation from the sample at block 120, to resonate in the chamber at block 130, irradiating or transmitting the scattered radiation from the chamber at block 140, and detecting the irradiated or transmitted scattered radiation at block 150. In one aspect, the method may be used in coordination with nucleic acid sequencing and may include identifying a single nucleic acid derivative in a sample received from a nucleic acid sequencing system in an effort to sequence a DNA or RNA molecule.

Figure 2:
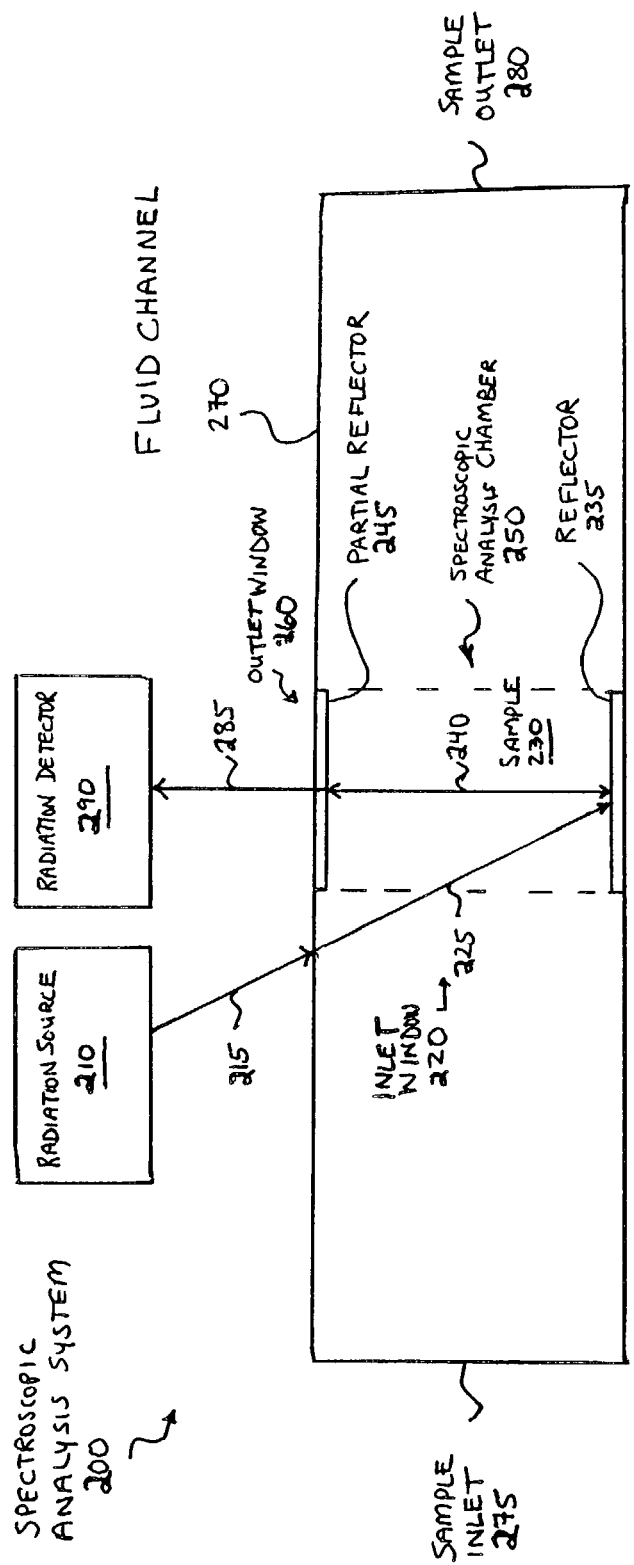
FIG. 2 shows a cross-sectional view of a spectroscopic analysis system containing a chamber in a fluid channel, according to embodiments of the invention.

FIG. 2 shows a cross-sectional view of a spectroscopic analysis system 200 suitable to perform a resonance enhanced stimulated Raman spectroscopic analysis of a sample in order to identify the sample, according to embodiments of the invention. The system includes an electromagnetic radiation source 210, a fluid channel 270, a spectroscopic analysis chamber 250 (shown by dashed lines), and an electromagnetic radiation detector 290. A sample 230 is contained within the chamber. During resonance enhanced spectroscopic analysis of the sample, the electromagnetic radiation source provides input or excitation radiation 215 to irradiate the sample within the chamber in order to generate an output of Raman inelastically scattered radiation 285 that contains information that may be used to characterize and identify the sample. In the case of stimulated Raman spectroscopy, the input radiation may be visible, ultraviolet, or near infrared spectrum radiation from an electromagnetic radiation source such as a laser and the output radiation may be corresponding stimulated Raman inelastically scattered radiation. The output radiation may be detected by the detector and used to identify the sample or one or more components thereof. b1

Initially, with reference to block 110, the sample 230, which may include a liquid, gas, or mixed fluid, is added to the chamber 250. In the system illustrated in FIG. 2, the sample is added to the chamber by flowing through the fluid channel. The channel is a void or hollowed-out space within a solid material and may be, for example, any tube, pipe, duct, or conduit to convey a fluid. The cross section of the channel may have a circular, oval, square, rectangular, or other shape. The fluid channel has a sample inlet 275 that is coupled with a sample source to receive a sample for analysis and a sample outlet 280 that is coupled with a sample destination to discharge an analyzed sample. The sample may be received at the inlet, flowed through the channel, flowed into the chamber, analyzed, subsequently flowed out of the chamber, and flowed through the outlet to the proper destination. Flow may be achieved by providing an appropriate driving force, such as a pressure differential between the inlet and the outlet or a pump within the channel. As one example, an aqueous solution of nucleic acid derivative may be received from a pressurized nucleic acid sequencing system by pressure injection and added to the chamber by flowing through the channel in order to identify the particular nucleic acid derivative. Alternatively, the sample may be added with a fluid pump, such as a syringe, through an opening to the chamber, rather than by flowing through a fluid channel, and subsequently removed with the syringe. In still other implementations, if the sample is electrically charged it may be added to the chamber under the force provided by an electric field, or if the sample is magnetic (e.g., has a magnetic moiety attached) it may be added to the chamber by the force provided by a magnetic field.

Although not required, the channel may be micro-sized. The term micro-sized channel, microfluidic channel, and the like will be used to refer to a channel having a cross-sectional length, for example a diameter in the case of a tubular pipe, which is less than approximately one millimeter (mm, one-thousandth of a meter). Often, the micro-sized channel may have a cross-sectional length that is in the range of approximately 10-500 micrometers (µm, one millionth of a meter). To help put these lengths in proper perspective, the cross-sectional diameter of a human hair is approximately 100 micrometers. These miniaturized channels are often useful for handling small sized samples and allow many channels to be constructed in a small substrate, although this is not a requirement.

Often, the channel and chamber may be disposed in a solid substrate. Suitable materials for solid substrates include but are not limited to ceramics (e.g., alumina), semiconductors (e.g., silicon or gallium arsenide), glasses, quartz, metals (e.g., stainless steel or aluminum), polymers (e.g., polycarbonate, polymethylmethacrylate (PMMA), polymethylsiloxine, polydimethylsiloxane (PDMS), or polytetrafluoroethylene (Teflon$^R$)), and combinations of these materials. Of course it will be appreciated that many other materials may also be used. Of these particular materials certain glasses, quartz, and polymers (e.g., PMMA and polycarbonate) are known to be substantially transparent at least in the visible spectrum. The transparency of these and other materials in the near infrared or ultraviolet is available in the literature or may easily be determined without undue experimentation. These transparent materials may be used as the substrate. Alternatively, non-transparent materials may be used as the substrate and transparent materials may be used as windows to allow sufficient transmittance of the relevant radiation. Materials that are suitable for windows include the transparent materials previously mentioned as well as other materials such as sapphire, magnesium fluoride, and calcium fluoride crystals. One exemplary substrate contains a channel and cavity formed in a stainless steel substrate, the channel and the cavity surfaces lined with an inert material such as Teflon^R for improved chemical compatibility), and one or more transparent windows of these or other transparent materials formed into the chamber to allow transmittance of radiation into the chamber. Alternatively, the stainless steel substrate may be replaced with glass, quartz, or ceramic, which should have sufficient compatibility with samples that omitting the Teflon coating would be appropriate. As yet another example, it may be desirable to use a polymer to help reduce fabrication costs and take advantage of molding, hot embossing, and other fabrication techniques. An exemplary substrate may include polydimethylsiloxane containing a channel and chamber housing molded or embossed therein into which one or more windows and reflectors may be inserted and affixed.

Various micromachining methods, such as micromilling, laser ablation, and focused ion beam milling may be used to form channels in ceramic, glass quartz, semiconductor, metal, and polymeric substrates. Approaches for fabricating microfluidic channels are described for example in U.S. Pat. Nos. 5,904,824, 6,197,503, 6,379,974, 6,409,900, and 6,425,972. Additionally, photolithographic etches that are commonly used in the semiconductor processing arts may be used to form channels in semiconductor, quartz, glass, and certain ceramic and metal substrates. For example, reactive plasma may be used to etch a channel having a depth of a few hundred microns and smooth vertical sidewalls in a silicon substrate. Photolithographic etches based on different chemistries may similarly be used to form channels in polymeric materials. In addition, molding, injection molding, stamping, hot embossing, and other approaches may be used to form channels in polymeric materials, as well as certain metals. Other techniques that are suitable for forming channels, as well as further background information on microfabrication is available in "The MEMS Handbook" (ISBN/ISSN: 0849300770), by Mohamed Gad-el-Hak, published on Sep. 27, 2001, containing pages 1-1368, and available from the University of Notre Dame.

A chamber according to embodiments of the invention contains a resonant cavity to contain a sample for analysis, at least one window to the cavity to transmit a first radiation having a first frequency (e.g., an input excitation radiation from a laser) into the cavity and to transmit a second electromagnetic radiation having a second frequency (e.g., an output beam of stimulated Raman radiation) out of the cavity, and a plurality of reflectors (e.g., multi-layer dielectric mirrors) affixed to a housing of the cavity to reflect radiation of a predetermined frequency (e.g., the stimulated radiation).

Referring to FIG. 2 and the particular chamber 250, the resonant cavity is a region within the fluid channel between a reflector 235 and a partial reflector 245. The chamber has an inlet opening, at the leftmost edge of the reflectors 235, 245 (as viewed), to allow addition of a sample, and an outlet opening, at the rightmost edge of the reflectors 235, 245 (as viewed), to allow removal of the analyzed sample. The sample may either be flowed continuously through the chamber or stopped within the chamber. Alternatively, the chamber may be located at a dead-end of the channel and may utilize a common inlet-outlet opening to add and remove a sample.

Once the sample is contained within the chamber, with reference to block 120 (FIG. 1), the sample is irradiated. In the system illustrated in FIG. 2, the source 210 provides input radiation 215 to the chamber and irradiates the sample positioned therein. Suitable sources include coherent light sources, lasers, light emitting diodes (LEDs), lamps, and fiber optic cables coupled with such a source of radiation. Radiation sources that provide strong monochromatic or quasimonochromatic radiation will often be favored over those that provide weaker or broad-spectrum radiation, since such monochromatic radiation facilitates detection of the relevant offset spectroscopic signals. The source 210 may contain filters or monochromators to reduce certain frequencies. The source may also contain lenses, mirrors, or other devices to redirect and focus the radiation on the chamber. These devices are commercially available from numerous sources, including vendors that are listed in "The Photonics Directory.υ.: The Photonics Buyers' Guide To Products and Manufacturers". This directory contains vendor listings for radiation sources, radiation detectors, spectrometers, spectroscopic analysis software, as well as numerous other accessories (e.g., lenses, wavelength selection devices, etc.). The Photonics Directory.TM. is available from Laurin Publishing, and is presently available online at the website: www.photonics.com/directory/index.asp.

A laser (light amplification by stimulated emission of radiation) may be used to provide a high intensity beam of coherent and monochromatic light having wavelengths suitable for resonance enhanced Raman spectroscopy. Many different types of lasers are suitable including tunable lasers, gas lasers, solid-state lasers, semiconductor lasers, laser diodes, VCSEL (Vertical-Cavity Surface-Emitting Laser), and quantum cavity lasers. The laser may be used to provide radiation at frequencies or wavelengths that are suitable for Raman spectroscopy, including radiation in the visible, often in the green, red, or near infrared, and ultraviolet regimes. Many molecules of potential interest, including many nucleic acid derivatives, have their resonance wavelengths in or near the ultraviolet spectrum. For example, adenine, a DNA base, has a near maximum resonance wavelength at approximately 267 nanometers (nm, one billionth of a meter). As such, the ultraviolet spectrum as an excitation wavelength may provide comparatively strong signals. Potential drawbacks to using ultraviolet as excitation radiation is that depending on the intensity it may damage the molecule of interest and may induce background noise from other system components and compounds that also have resonance wavelengths in the ultraviolet. Lasers and associated optics for the ultraviolet range also tend to be more costly. Another option is the use of near infrared or visible excitation radiation. While the signals may be slightly less intense compared to ultraviolet, there may be comparatively less background noise, since most materials have their resonance wavelengths outside of these spectral frequencies. Although this particular laser is not required, the present inventors have utilized an argon-ion laser to provide a radiation at about 514 nanometers wavelength and have found that such a laser is suitable for differentiating the Raman spectra of DNA nucleotides. This particular laser is commercially available from Coherent Inc. of Santa Clara, Calif. and Spectra-Physics, Inc. of Mountain View, Calif. The laser may be operated at a sufficient intensity that allows detection and avoids damaging the molecule. As an example, the laser may be operated at energy in the range of approximately 100 W to 100 kW, depending upon the stability of the molecule. Other suitable lasers include a 10 mW helium-neon laser providing radiation at a wavelength of 633 nanometers, a linearly polarized 50 mW diode laser providing radiation in the near infrared at a wavelength of 785 nanometers, and other lasers.

Referring to FIG. 2, the chamber receives input radiation from the source through at least one window into the cavity that allows the sample positioned therein to be irradiated. The particular chamber illustrated receives transmitted radiation 225, which is transmitted through the fluid channel walls, through an inlet window 220 opening to the cavity at a left edge of the reflectors 235, 245. The inlet window may be a portion of the cavity housing that is at least partially transparent to the particular excitation radiation, a position adjacent to a reflector, a space or gap between reflectors, an incomplete or finite reflector through which a portion of the radiation may pass, a lens, an electro-optic device, or a waveguide (e.g., a fiber optic material or wispering gallery mode) that confines directs and guides the radiation into or out of the cavity. Suitable electro-optic devices include laser modulators and Pockel cells. A Pockel cell is a solid state electro-optic device that is often used as a Q-switch. An electrical field or other signal is applied to the device in order to modify or switch the birefringence of the cell. This allows modifying the transmittance of radiation through the cell and switching it on or off. Accordingly, the electro-optical device may act as a window that may be opened or closed by applying appropriate electrical current in order to allow transmittance of light through the device into and/or out of the chamber. Electro-optic devices and Pockel cells are available commercially from Conoptics, Inc. of Danbury Connecticut, among other vendors. It is also contemplated that an actual moving shutter may be opened and closed to allow light into and/or out of the chamber. Hinged members commonly used in MEMS (micro-electromechanical) devices may be used for the shutter.

Figure 3:
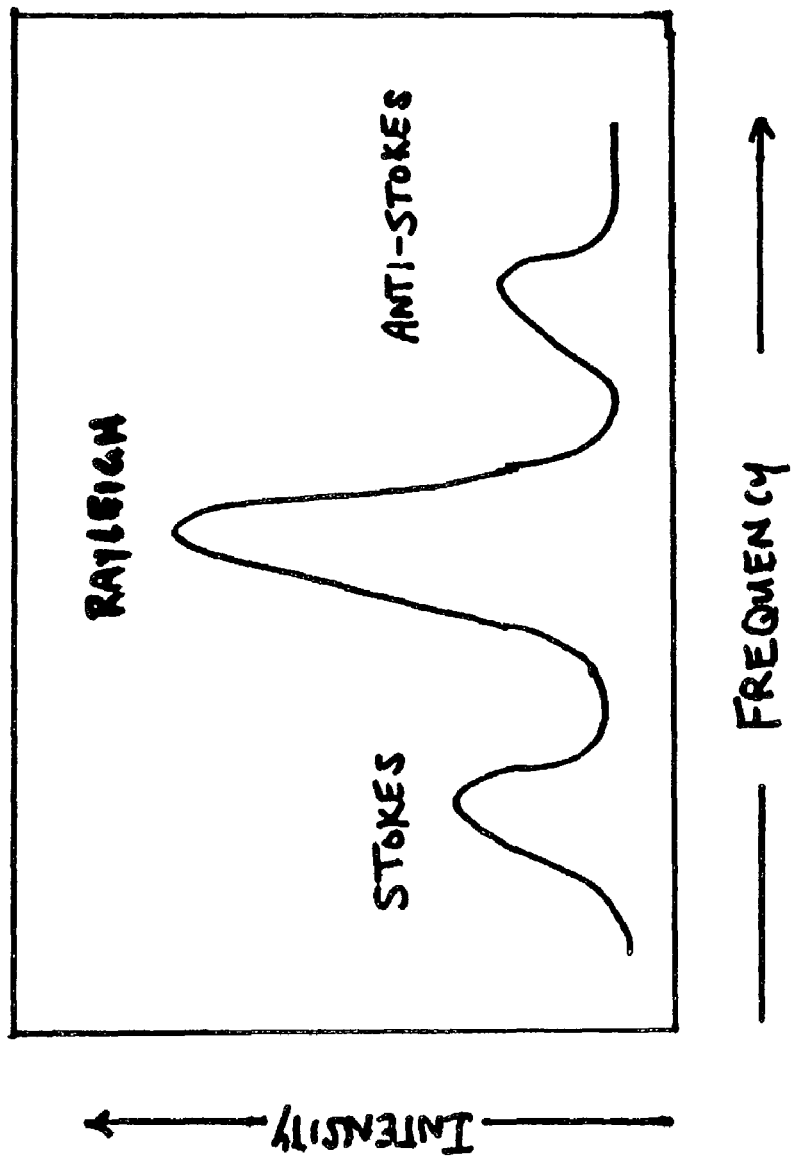
FIG. 3 shows Rayleigh, Stokes, and anti-Stokes radiation.

As previously discussed, the transmitted input radiation 225 is introduced into the cavity and some of the input radiation, or some of the reflected input radiation, or both, irradiates the sample. With reference to block 130 of FIG. 1, some of the radiation is scattered by the sample. As used herein, the terms "scattered radiation" and the like will be used to refer to a photon of light or other radiation that has collided with and been absorbed by sample matter, such as a molecule, and has been released or emitted. Most of the scattered photons will be released elastically in which the scattered radiation has no change of energy or frequency. This radiation is known as Rayleigh scattered radiation. Some of the scattered photons, often a small fraction, will be released inelastically in which there is an exchange of energy and a change of frequency. These are well-known phenomenon. Stokes scattered radiation refers to scattering where the molecule loses energy and the frequency is reduced whereas anti-Stokes scattered radiation refers to scattering where the molecule gains energy and the frequency is increased. This scattering of light by matter is known as Raman spectroscopy. FIG. 3 conceptually illustrates Rayleigh, Stokes, and anti-Stokes radiation. Stokes and anti-Stokes radiation typically have lower intensity than Rayleigh radiation, and respectively exist at lower and higher frequencies than Rayleigh radiation. As used herein, Stokes and anti-Stokes radiation will be referred to collectively as inelastically scattered radiation.

The change in frequency or wavelength of the inelastically scattered radiation is based on the particular characteristics of the sample or molecule of interest contained therein. That is, the difference between the frequencies of the input radiation and the inelastically scattered radiation is characteristic of the sample. For example, the frequency of a photon scattered from an inelastic collision with a molecule may depend upon the polarization, vibration, rotation, and orientation characteristics of a molecule. The reasons for this are explained by quantum mechanics. Briefly, the photon may excite the molecule from its ground vibrational state to a high-energy or virtual vibrational state, from which it may relax to a lower-energy vibrational state by emission of inelastically scattered radiation, and ultimately relax back to the ground state. Further background information on this process as well as further background information on other vibrational spectroscopy topics is available in "The Handbook of Vibrational Spectroscopy", by John Chalmers and Peter R. Griffiths, published by John Wiley & Sons, Ltd. In any event, the frequency shifts in the light that is inelastically scattered by a molecule of interest incorporate information comprising a fingerprint or signature for the molecules polarization, vibration, rotation, and orientation characteristics.

As previously discussed, it is often difficult and improbable to detect, or reliably detect, spontaneously scattered radiation from a dilute molecule in solution. Accordingly, with reference to block 130 of the method 100 of FIG. 1, the present inventors have discovered systems and methods for resonating radiation in a cavity in order to perform a resonance enhanced spectroscopic analysis of a sample. The resonated signal is stronger and easier to detect than the spontaneous signal. Advantageously, this may allow improved probability and reliability of accurately and reliably detecting and identifying dilute molecules of interest in solution.

The particular chamber 250 of FIG. 2 is a resonate chamber containing the reflector and the partial reflector to confine and resonate a radiation within the cavity in order to increase or amplify its intensity. The inelastically scattered radiation may be resonated in order to increase its intensity and aid detection and identification of a sample positioned within the chamber. The reflectors may be incorporated into or affixed to the housing of the channel to internally reflect radiation within the cavity. Radiation that is inelastically scattered by the sample or a portion of the input radiation 225 that is reflected by the reflector 235 may be reflected by the partial reflector 245 and resonated in the cavity. Portions of the radiation that are not reflected sufficiently parallel to the optical axis normal to the reflectors may leave the chamber quickly. The reflectors may have lengths that are smaller than the distance of separation between the reflectors to allow rapid removal of misaligned radiation. In this way, in addition to resonating a particular frequency or range of frequencies, the chamber effectively selects a direction of radiation that accumulates in the chamber, thereby allowing an intense, coherent beam of radiation.

The cavity may have a shape and size that facilitates resonance. As illustrated, chamber 250 has the reflectors opposite and parallel to one another, centered along a common optical axis, and separated by a particular predetermined distance that is proportional to or at least based on a wavelength of radiation to be resonated in the chamber, and that provides a nondestructive relationship between the phases of incident and reflected radiation. When the distance between the reflectors is a multiple of approximately half the wavelength of the radiation field, the partial waves may overlap substantially constructively, otherwise they may overlap less constructively or destructively. The particular reflectors may be separated by a distance that is approximately one half the product of the mode of the resonance frequency, times the speed of light, divided by the index of refraction of the medium filling the cavity, divided by the frequency of the particular radiation to be resonated in the chamber. Since coherent Raman spectroscopy may utilize excitation radiation in the visible, near infrared, and ultraviolet regimes, and since the inelastically scattered radiation is merely offset from the excitation radiation, the cavity may be designed to resonate inelastically scattered radiation having virtually any wavelength in the visible, ultraviolet, and near infrared regimes, depending upon the particular excitation radiation desired. The particular choice of excitation radiation may depend upon the cost of the laser and detectors, the capability of the detectors to detect a particular radiation, the resonance and stability of the molecule of interest, the false signals or noise caused by other absorbing molecules or species that are not of interest, etc.

A chamber may be designed to resonate an inelastically scattered radiation for a molecule of interest (e.g., a particular nucleotide) or set of molecules of interest (e.g., a set of nucleotides). As one example, consider for a moment the Stokes spectra shown in FIG. 4 (which will be discussed in more detail below) generated from excitation with a 514 nanometer argon-ion laser. The bottommost spectra for the molecule deoxythymidine monophosphate has a pronounced peak at a Stokes Raman shift of approximately 1350 cm−1. This shift is offset from the excitation wavenumber of 19455 cm$^{-1}$ (i.e., $10^7/514=19455$) for the 514 nanometer excitation radiation, and translates into an actual Stokes Raman wavenumber of approximately 18105 cm$^{-1}$ (i.e., 19455-1350). This corresponds to a wavelength of 552 nanometers (i.e., $10^7/18105$). This Stokes scattered radiation may be resonated in the chamber in order to amplify the optical signal and improve detection. The particular reflectors shown in FIG. 2 may be separated by a distance that is approximately one half the product of the mode of the resonance frequency times the speed of light divided by the index of refraction of the medium filling the cavity divided by the frequency of the particular radiation to be resonated in the chamber for this 552 nanometer scattered radiation. As another example, the chamber may be designed to resonate this wavelength of radiation as well as wavelengths of inelastically scattered radiation from other molecules of interest. In one embodiment of the invention, the predetermined distance between the reflectors is a function of wavelengths corresponding to prominent peaks in the Raman spectra of a plurality of molecules of interest (see e.g., the peaks in FIG. 4). The function may be an average, a weighted average, or other combinatorial functions.

The reflector 235 and the partial reflector 245 may be multiple layer dielectric mirrors, metal mirrors, or other reflectors that are commonly utilized in the spectroscopy, laser, optics, or fiber optic arts. A multi-layer dielectric mirror, of which a Distributed Bragg Reflector (DBR) is one example, is an interference based mirror structure containing a stack or laminate of alternating layers of materials having different indices of refraction. The thickness of the layers may be proportional to the wavelength of the radiation to be reflected such that the reflected waves from the layers are in phase with one another and superimpose. The reflector may contain alternating layers of low and high refractive index materials. A dielectric or insulating material is often used for at least one of the alternating layers and the other layer may be a different dielectric material, a non-dielectric material, a semiconductor, or other materials. One non-limiting example of a dielectric mirror includes a plurality of alternating layers of silicon (Si) and an oxide of silicon (e.g., silicon dioxide, $SiO_2$), for example $SiO_2/Si/SiO_2$ that each have a thickness approximately quarterwavelength (i.e., ¼ the wavelength) of the reflected radiation (e.g., inelastically scattered radiation). More pairs of alternating layers may be added to improve reflectance. The partial reflector 235 may have less total layers than the reflector 245 in order to transmit relatively more incident radiation than the reflector 245. Another non-limiting example of a dielectric mirror includes a quarterwavelength thickness of gallium arsenide (GaAs), a stress matched $SiO_2/Si_3N_4/SiO_2$ trilayer (alternating dielectric layers), and about 1500 Angstroms of gold. That is, this mirror contains both a dielectric interference based mirror as well as a metal mirror. Numerous other examples of multi-layer dielectric mirrors abound in the literature. Multi-layer dielectric mirrors may achieve high reflectance that are often in the range of approximately 99-99.9%, or higher. These mirrors may be used to rapidly achieve good gains and increased intensities.

A multi-layer dielectric mirror may contain layers that have a thickness that is proportional to a wavelength of an inelastically scattered radiation for a molecule of interest (e.g., a particular nucleotide) or set of molecules of interest (e.g., a set of nucleotides). For example, the layers may have a thickness that is approximately quarterwavelength of the average anti-Stokes or Stokes scattered radiation for a set of monobasic nucleic acid derivatives for DNA. This may allow a single resonant cavity to be used to perform resonance enhanced spectroscopic analysis of the entire set of derivatives, for example in the context of DNA sequencing; and allow identification of a particular derivative of the set based on a resonance intensified beam incorporating derivative specific frequency shift information that is, transmitted from the cavity. As another example, the layers may have a thickness that is approximately quarterwavelength of the 552 nanometer Stokes scattered radiation for molecule deoxythymidine monophosphate exposed to 514 nanometer radiation from an argon-ion laser. Other thicknesses may apply for other molecules and excitation radiations.

Multi-layer dielectric mirrors are available commercially from a number of sources or may be fabricated. SuperMirrors™ are examples of suitable multi-layer dielectric mirrors that are available from Newport Corporation of Irvine, Calif. The SuperMirrors™ may be obtained and affixed to the housing of the chamber. Alternatively, a multi-layer dielectric mirror may be fabricated by techniques that are commonly used in the semiconductor processing arts (see e.g., U. S. Pat. Nos. 6,320,991 or 6,208,680). As another example, a dielectric mirror containing alternating layers of Si and $SiO_2$ may be deposited by a conventional chemical vapor deposition or physical vapor deposition technique that is commonly used in the semiconductor processing arts. For example, a low pressure chemical vapor deposition (LPCVD) technique may be used to provides good quality layers of controlled thickness. Alternatively, a physical vapor deposition technique such as evaporation, sputtering, or molecular beam epitaxy may be used to deposit the layers. As another variation, a thicker silicon layer may be deposited by a chemical vapor deposition and a silicon dioxide layer may be thermally grown from the silicon layer to a similar thickness. Of course, the chemical and physical deposition techniques may also be used to deposit other materials.

The reflector and partial reflector may alternatively be metal mirrors. Suitable metals include, among others, aluminum, gold, silver, chrome, and alloys, mixtures, or combinations thereof. Hereinafter the term metal will include pure metals as well as alloys, mixtures, or combinations. Suitable metal mirrors are available from Newport Corporation. Metal mirrors may also be fabricated by conventional chemical vapor deposition and physical vapor deposition techniques. For example, a gold layer may be deposited on a cavity wall by molecular beam epitaxy evaporative deposition. Metal mirrors may provide reflectance in the range of approximately 90-95%, or slightly higher but usually not greater than about 99%.

The reflected radiation may be resonated within the cavity and may stimulate or induce other inelastic scattering events. The stimulated events may occur more rapidly or more probabilistically than spontaneous scattering events and the intensity of the inelastically scattered radiation may build within the chamber until saturation or equilibrium is achieved wherein round trip gain due to resonance matches loses. It is anticipated that intensities up to on the order of a hundred milliwatts may be obtained. Such resonance enhanced stimulated Raman spectroscopy may provide an amplified, intense, coherent, frequency-shifted beam that should allow probable, accurate, and reliable detection and identification of even a single molecule of interest in dilute solution. It is not required that a single molecule of interest be analyzed and in other embodiments a sample containing any desired number of molecules of interest may be analyzed.

By now it should be apparent that different types of samples may be analyzed. As used herein, the term sample will refer to one or more molecules, atoms, or ions to be analyzed either alone or with a vapor, gas, solution, solid, or sorbent (e.g., a metal particle or colloidal aggregate). The sample may contain a dilute solution containing one or more molecules of interest. Virtually any molecule may be of interest, depending on the particular implementation, such as a biologic molecule, a molecule associated with nucleic acid sequencing, a pharmaceutical, pesticide, an herbicide, a polymer, a pollutant, or others. For example in the case of analyzing a biological molecule of interest associated with nucleic acid sequencing, an aqueous or other solution containing a protein, protein fragment, or nucleic acid derivative may be analyzed. The term nucleic acid derivative will be used to refer to a nucleic acid, nucleic acid fragment, nucleotide, nucleoside (e.g. adenosine, cytidine, guanosine, thymidine, uridine), base (e.g. adenine, cytosine, guanine, thymine, uracil), purine, pyrimidine, or a derivative of one of these molecules. One exemplary sample contains a solution of a single nucleic acid derivative having a single base that is selected from the group consisting of adenine, cytosine, guanine, thymine, and uracil.

Proteins provide a number of critical reactions, structures, and controls for cells. Nucleic acids provide cells information about which proteins to synthesize. Nucleic acids are linear polymers of nucleotides connected by phosphodiester bonds. Nucleic acids may be deoxyribonucleic acid (DNA) or ribonucleic acid (RNA). Nucleotides consist of three parts, a phosphate group, a pentose (a five carbon sugar molecule), and a base. Nucleosides are bases and sugars without a phosphate group. The bases of both nucleotides and nucleosides are adenine (A), cytosine (C), guanine (G), thymine (T), and uracil (U). The bases adenine, cytosine, and guanine are found in both DNA and RNA, thymine usually found only in DNA, and uracil is usually found only in RNA. Accordingly, the nucleosides for DNA include deoxyadenosine, deoxyguanosine, deoxycytidine, and deoxythymidine, whereas the nucleosides for RNA include adenosine, guanosine, cytidine, and uridine. Likewise, the nucleotides for DNA include deoxyadenosine monophosphate, deoxyguanosine monophosphate, deoxycytidine monophosphate, deoxythymidine monophosphate (or in the salt form, deoxyadenylate, deoxyguanylate, deoxycytidylate, and thymidylate), whereas the nucleotides for RNA include adenosine monophosphate, guanosine monophosphate, cytidine monophosphate, uridine monophosphate (or in the salt form, adenylate, guanylate, cytidylate, and uridylate). In RNA the pentose is ribose whereas in DNA the pentose is deoxyribose. The bases cytosine, thymine, and uracil are pyrimidine bases and contain a single heterocyclic ring containing carbon and other atoms, in this case nitrogen. The bases adenine and guanine are purine bases and contain a pair of fused heterocyclic rings that also contain nitrogen. The ability to determine a nucleic acid and/or protein sequence may have tremendous commercial importance in the fields of medical diagnosis, treatment of disease, and drug discovery. Of course, these are just examples of the types of samples and molecules that may be analyzed by the systems and methods developed by the present inventors.

With continued reference to the method 100 of FIG. 1, and to block 140, after resonating, the scattered radiation may be irradiated or transmitted from the chamber. Referring to FIG. 2, the chamber may contain at least one window to allow the radiation to exit the chamber and be detected. The particular chamber 250 contains an outlet window 260, which in this particular instance comprises the partial reflector 245. The partial reflector is an incomplete or finite reflector that has a sufficient reflectivity to achieve resonance and a sufficient transmittance to allow a detectable level of incident radiation to be transmitted to the detector 290. The reflector 235 may have a higher total reflectance than the partial reflector 245 in order to provide good amplification of intensity in the cavity, although this is not required. In one instance, the reflector 235 may have a high reflectivity for both the input excitation radiation and the inelastically scattered radiation, for example greater than approximately 99% (e.g., approximately 99.9%) for both, whereas the partial reflector 245 may have a sufficient transmittance for the inelastically scattered radiation, for example a transmittance that is not less than approximately 1% (or a reflectance that is not greater than approximately 99%). Of course alternate types of outlet windows may also be used, such as a transparent material incorporated into the cavity housing, a Pockel cell, a space, gap, slit, pinhole, or other opening in the reflector 235, or a shutter. Additionally, as another alternative, a single inlet-outlet window may be utilized to transmit radiation into and out of the chamber.

At least a portion of the resonated radiation 240 that is incident on the partial reflector 245 leaves the cavity and chamber as output radiation 285. The output radiation contains inelastically scattered radiation that incorporates frequency-shift information about the sample in the chamber. The intensity of the output radiation may depend upon the reflectivity of the partial reflector, the resonance characteristics of the chamber, and upon losses due to absorption, scattering and diffraction. Often, the chamber will be designed to achieve high intensities of the output radiation to allow accurate detection and identification of samples.

With reference again to the method 100 of FIG. 1, at least some of the inelastically scattered radiation in the output radiation 285 is detected at block 150. The electromagnetic radiation detector 290 is shown in simplified format and is to be interpreted broadly. Often, the output radiation may be passed through a lens and a wavelength selection device. The lens may collect, direct, and focus the radiation emitted from the chamber. The light from the lens or from the chamber may be passed through a wavelength selection device that emphasizes, selects, separates, or isolates a particular frequency or range of frequencies. The wavelength selector may be used to distinguish radiation of interest (e.g., inelastically scattered radiation) from other radiation (e.g., elastically scattered radiation and excitation radiation). Suitable wavelength selection devices include among others prisms, monochromators, filters (e.g., absorbance, bandpass, interference, or Fourier), dichroic filters, dichroic mirrors, and demultiplexers.

After passing the radiation from the chamber through any lenses, wavelength selection devices, and the like, the resultant radiation may be passed to a spectrometer, optical multi-channel analyzer (OMA), or other radiation detection device. These radiation detection devices will often employ an optical transducer to convert received radiation into a corresponding electrical signal that captures and represents at least some of the same information. Exemplary optical transducers include a charge coupled device (CCD), phototransistor, photomultiplier tube, photo diode, or an array of one or more of these devices.

The radiation detection device may comprise a Raman spectrometer. Spectrometers are well known radiation detection devices that measure the wavelength and intensity of light. Spectrometers are commercially available from a number of sources. One suitable Raman spectrometer is Spectra-Pro 300i Spectometer available from Acton Research Corporation of Acton Mass. Another spectrometer that is suitable is the RAMANRXN1 Analyzer available from Kaiser Optical Systems, Inc. (website: www.kosi.com/) of Ann Arbor, Mich. This spectrometer uses a thermoelectrically cooled Charge Coupled Device (CCD) array to provide high sensitivity detection of radiation. Optionally, this spectrometer may also be obtained with an Invictus NIR Laser as a radiation source, a SuperNotch® Filter, a Holographic Laser Bandpass Filter, and a HoloSpec holographic imaging spectrograph. Further background information about this spectrometer including its operation is available from the vendor. Of course other spectrometers may also be used.

Figure 4:
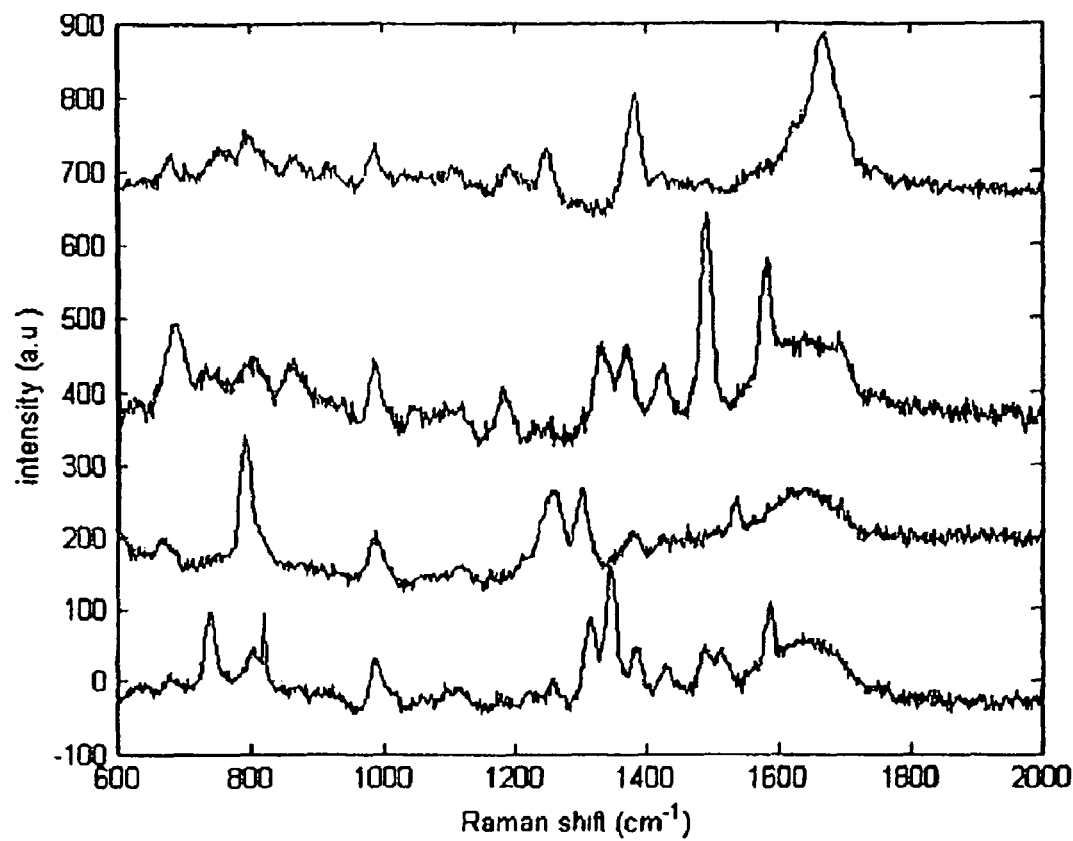
FIG. 4 shows Stokes Raman spectra for dilute aqueous solutions of four DNA nucleotides, according to embodiments of the invention.

Often, the spectrometer may generate spectra showing frequency or wavelength versus intensity. FIG. 4 shows Stokes Raman spectra for highly diluted aqueous samples of each of the four DNA nucleotides, according to embodiments of the invention. For clarity, the four spectra have been offset or displaced from one another along the vertical axis. From top to bottom, the spectra are for deoxyadenosine monophosphate, deoxycytidine monophosphate, deoxyguanosine monophosphate, and deoxythymidine monophosphate. The spectra were generated by performing spontaneous Raman spectroscopic analysis on the samples including irradiating the samples with 514 nanometer radiation from a laser and detecting the output inelastically scattered radiation with a Raman spectrometer. The spontaneous spectra should be substantially similar to resonance enhanced Raman spectra except that the signals would be correspondingly weaker in intensity. The figure shows intensity in arbitrary units versus Raman wavelength shift (Stokes offset from the excitation radiation) in reciprocal centimeters. As shown, each of the spectra have distinct spectral characteristics, prominent peaks, or fingerprint bands, that identify the corresponding nucleotide. Exemplary prominent peaks include 1630 $cm^{-1}$ for the top spectra, 1440 $cm^{-1}$ for the next spectra down, 800 $cm^{-1}$ for the second spectra from the bottom, and 1350 $cm^{-1}$ for the bottom spectra.

Finally, with reference to the method 100 of FIG. 1, the sample may be identified at block 160. The sample may be identified by comparing the determined spectrum with a spectral library containing many predetermined spectrum for known samples and identifying the sample as one of the known samples if the determined spectrum sufficiently approximates the corresponding predetermined spectrum in the library. The electrical signals generated by the radiation detector as a result of the output radiation may be provided to a computer system that is appropriately programmed with spectroscopic analysis instructions and the library (e.g., a database) that allows the Raman fingerprint or signature represented in the electrical signals to be correlated to a specific fingerprint or signature in the library. For example, in the case of a spectrometer, a spectrum (or certain bands thereof) for a sample may be compared or contrasted to spectroscopic data for other identified samples to determine whether the fingerprints are sufficiently identical (i.e., the sample has the same identity as the identified sample in the database). Various methods for identification of nucleotides by Raman spectroscopy are known in the art (see e.g., U.S. Pat. Nos. 5,306,403, 6,002,471, or 6,174,677). The identity of the sample may be stored in memory, further analyzed, or used for other purposes.

With reference again to the method 100 of FIG. 1, another way of implementing this method may include adding a sample to a chamber at block 110, irradiating the sample with a short and accurately-known pulse of a radiation having substantially the same frequency or wavelength as an inelastically scattered wavelength relevant to the sample at block 120, then scattering, resonating, and irradiating or transmitting the radiation from the cavity at blocks 130-140, respectively, and then detecting the radiation as well as some indication of the decay time of the inelastically scattered light in the chamber at block 150. The decay time may be used as a fingerprint or signature for the identity of the sample. Of course other methods are also contemplated.

Figure 5:
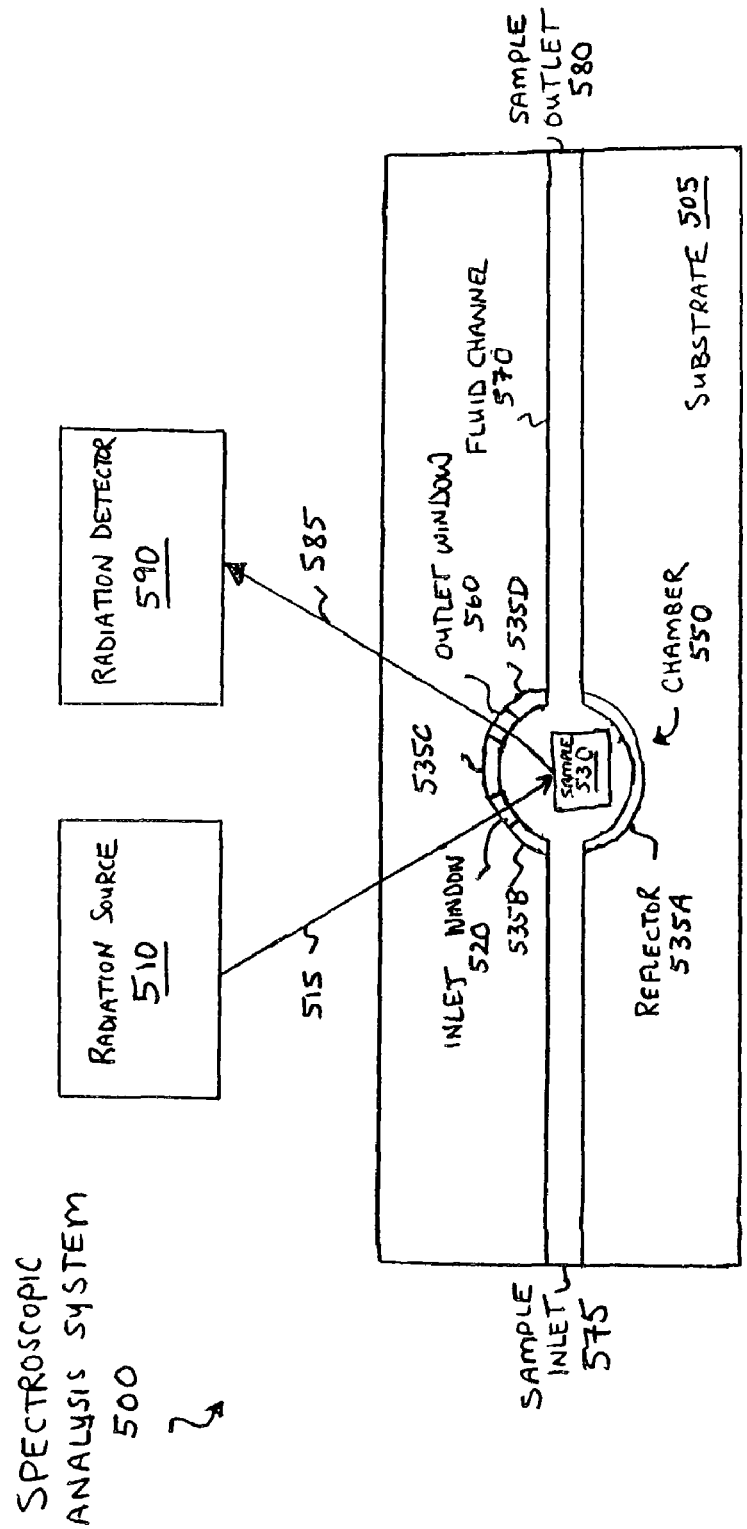
FIG. 5 shows a cross-sectional view of a spectroscopic analysis system containing a spheroidal chamber coupled with a fluid channel, according to embodiments of the invention.

FIG. 5 shows a cross-sectional view of a spectroscopic analysis system 500 suitable to perform a resonance enhanced spectroscopic analysis of a sample in order to identify the sample, according to embodiments of the invention. The system includes a radiation source 510, a substrate 505, a fluid channel 570, a spectroscopic analysis chamber 550, and a radiation detector 590. A sample 530 is contained within the chamber. The channel and the chamber are formed within the substrate and are coupled. The particular chamber contains a spheroidal resonant cavity, an inlet window 520, a first, second, third and fourth curved reflectors 535A-D, and an outlet window 560. The sample may be added to the channel at an inlet 575 thereof, then flowed into a cavity of the chamber and spectroscopically analyzed, and then flowed out of the chamber and through the sample outlet 580.

The spheroidal resonant cavity is formed of concave surfaces that may assist with reflecting radiation toward the interior of the cavity. The term spheroidal will be used to refer to a shape that resembles or approximates a sphere but that is not necessarily a perfect sphere. Of course, the spheroidal shape is not required and in other cavities only a portion of the chamber housing may be concave (e.g., spherically or parabolically concave), or the cavity may be a cylindrical void (e.g., having a diameter greater than that of the fluid channel), a polyhedron void, a hexahedron void, a cubic void, or a void having any other regular or irregular shape.

The cavity serves as a wide spot in the fluid channel and may have a volume that is convenient for the particular implementation. Typically, the cavity will have a volume that is not greater than about a milliliter (mL, one-thousandth of a liter). Alternatively, if a smaller cavity is favored, the cavity may be a micro-sized cavity or microcavity having a volume that is not greater than approximately a microliter (μL, one-millionth of a liter). For example, the volume may be approximately 500 nanoliters (nL, one billionth of a liter), approximately 100 nL, approximately 1 nL, or less.

An input excitation radiation 515 from the source 510 is directed through the substrate, through the inlet window 520, and into the cavity. The particular inlet window 520 comprises a region of the cavity housing between the second and third reflectors 535B-C that is at least partially transparent to the inlet radiation 515. The inlet window may be a space between the second and third reflectors, for example a portion of sufficiently transparent substrate, or a partial reflector between the second and third reflectors or a transparent material. At least some of the input radiation irradiates the sample and is inelastically scattered. The reflectors 535A-D confine the inelastically scattered radiation, and in this particular embodiment much of the input radiation, inside the chamber by internal reflection. Some of the reflected radiation may stimulate further inelastically scattered radiation by re-irradiating the sample and again being inelastically scattered. In another embodiment of the invention, such as that discussed in FIG. 8, an outlet window may be used to remove the input excitation radiation from the cavity.

Output radiation 585 leaves the cavity through the outlet window 560 and contains at least some resonance enhanced stimulated inelastically scattered radiation. The outlet window is positioned away from the path of the input radiation, and primary reflections thereof, to reduce transmission of the inlet radiation through the outlet window. Of course, this is not required, and a wavelength selection device may be used to remove any such radiation that is transmitted.

Figure 6:
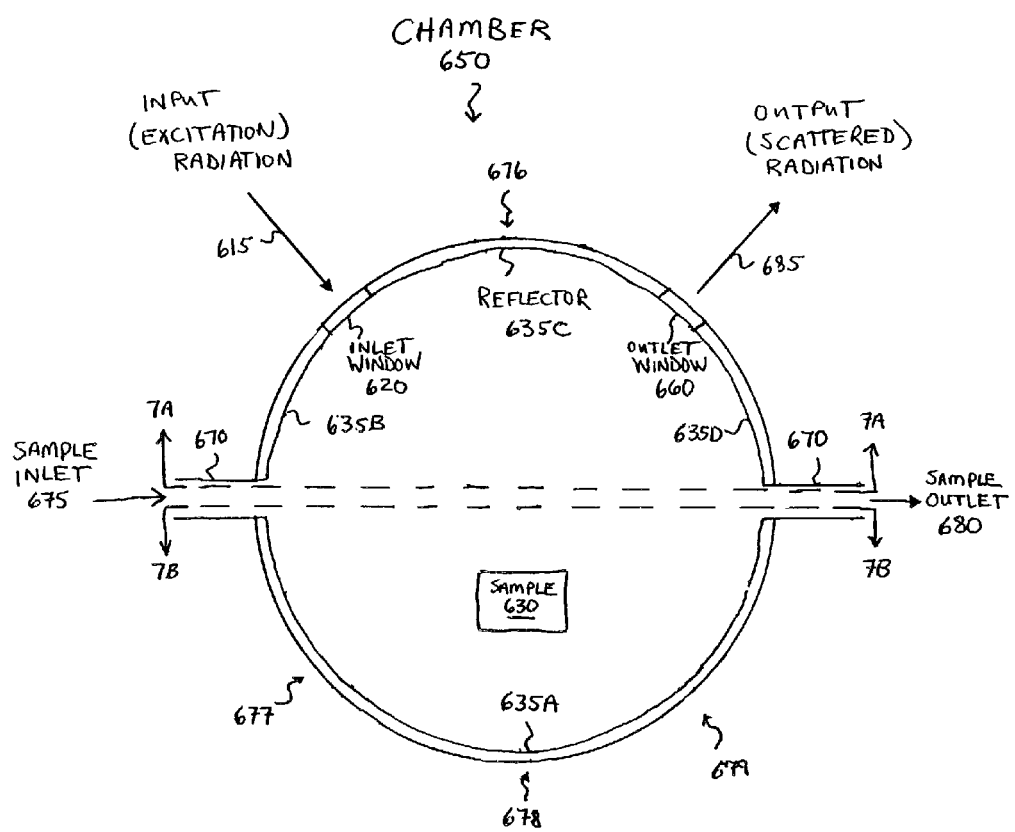
FIG. 6 shows another cross-sectional view of a spheroidal chamber coupled with a fluid channel, according to embodiments of the invention.

FIG. 6 shows another cross-sectional view of a spheroidal chamber 650, according to embodiments of the invention. The chamber shows the features of the chamber 550 as well as alternate locations 676, 677, 678, and 679 for either the inlet window 620 or outlet window 660. By way of example, the outlet window may be re-positioned at one of the locations 676-679, or the inlet window may be re-positioned at one of the locations 676-679. A sample 630 is positioned within the chamber. FIG. 6 also shows section lines 7A-7A and 7B-7B that respectively show the views of FIGS. 7A and 7B.

Figure 7A:
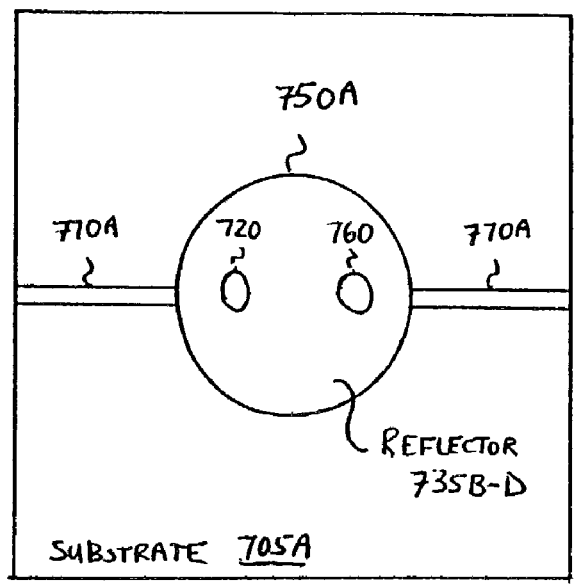
FIG. 7A shows a view of the top of the chamber shown in FIG. 6 along the section lines 7A-7A, according to embodiments of the invention.
Figure 7B:
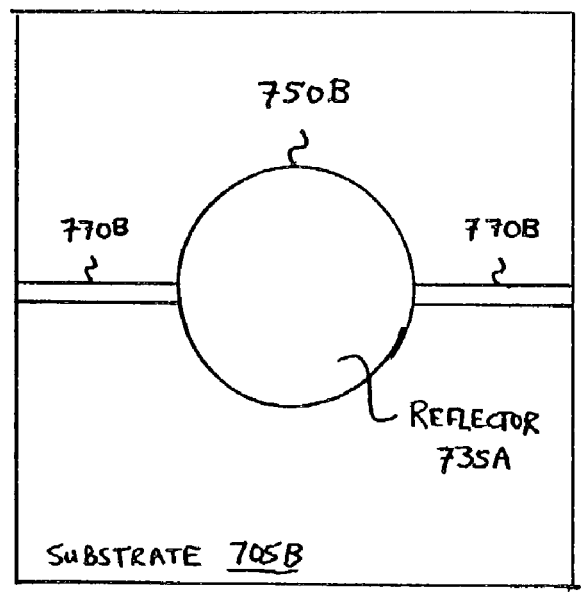
FIG. 7B shows a view of the bottom of the chamber shown in FIG. 6 along the section lines 7B-7B, according to embodiments of the invention.

FIGS. 7A-7B show fabrication of the chamber 650 of FIG. 6, according to embodiments of the invention. FIG. 7A shows a top-plan view of the top of the chamber 650 along the section lines 7A-7A shown in FIG. 6. The hemi-spheroid void 750A of the top of the chamber 650 and the hemi-cylindrical voids 770A (half of a cylindrical channel void) may be formed within a substrate 705A. In one example, these voids 750A, 770A may be formed in a quartz or glass substrate by photolithography and etching. An anisotropic etch with agitation may be used to form the nearly spherical concave surfaces of the chamber 750A and the concave cylindrical surfaces of the channel 770A by etching along crystal planes. In another example, these voids may be formed in a polymeric material, such as PDMS by molding or embossing.

The interior surface of the hemi-spheroid void 750A contains reflectors 735B-D (which correspond to the reflectors 635B-D in the view of FIG. 6). The reflector may be formed by subsequent alternating deposition of layers of appropriate thickness of materials having different index of refraction (e.g., Si and $SiO_2$). The depositions may be over the whole hemisphere in which case an inlet window 720 and an exit window 760 may be formed by removing a portion of these deposited layers to form a partial reflector, or by removing all of these layers to form a transparent quartz window. These layers may be removed by laser ablation, by etching, or by other conventional techniques for removing layers. Alternatively, a mask patterned with the sizes and positions of the windows 720 and 760 may be used to selectively deposit the multi-layer dielectric mirror layers over the non-window portions. In the case of the PDMS polymer, a sapphire, quartz, or other transparent window may be molded into the polymer or the polymer drilled and the window fixedly inserted.

FIG. 7B shows a top-plan view of the bottom of the chamber 650 along the section lines 7B-7B shown in FIG. 6. The hemi-spheroid void 750B of the bottom of the chamber 650, the hemi-cylindrical voids 770B, and the reflector 735B may be formed within a substrate 705B, such as a silicon substrate, as described for FIG. 7A. After forming these structures, the substrate 705A may be bonded to the substrate 705B by a wafer bonding approach, for example by a high temperature fusion of oxidized surfaces thereof, or with an adhesive.

Figure 8:
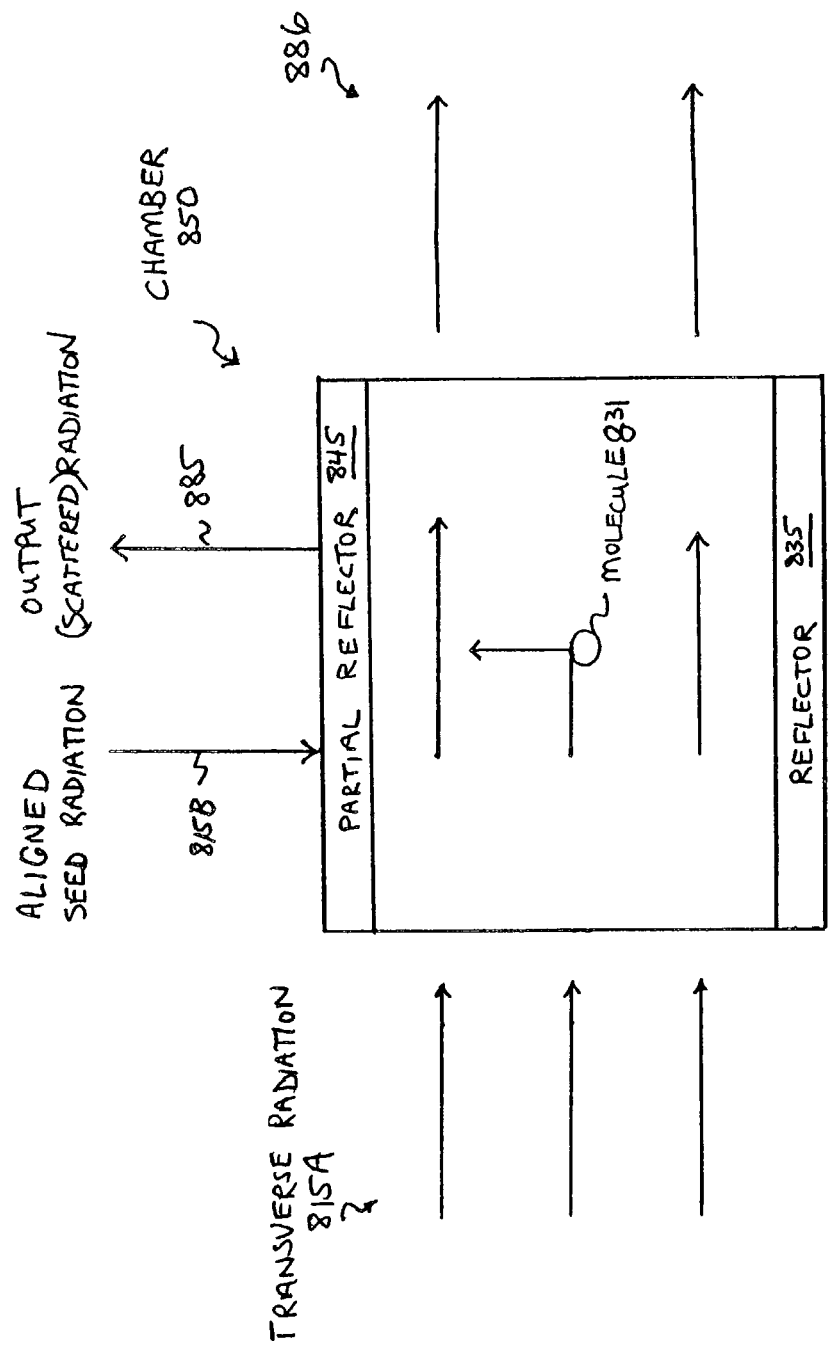
FIG. 8 shows a top-plan view of a spectroscopic analysis chamber configured to receive excitation radiation in the form of aligned frequency-matched seed radiation having the same frequency as the scattered radiation, and transverse frequency-unmatched radiation having a different frequency than the scattered radiation, according to embodiments of the invention.

FIG. 8 shows a top-plan view of a spectroscopic analysis chamber 850 configured to receive input excitation radiation in the form of aligned seed radiation 815B and transverse radiation 815A, according to embodiments of the invention. The input transverse excitation radiation may have any suitable frequency. The direction of the transverse radiation is crosswise, perpendicular, to the direction of the output radiation 885, and to the direction of resonance. This allows a portion of the transverse radiation 886 that does not irradiate a molecule 831, to leave the chamber. This may aid in detecting the output inelastically scattered radiation 885. The seed radiation is added to the chamber through a partial reflector 845. The seed radiation may have the same frequency as radiation inelastically scattered from a particular sample and may stimulate scattering if that sample is contained within the chamber. The direction of the seed radiation is opposite, but aligned with, the direction of output inelastically scattered radiation 885. This allows the seed radiation transmitted through the partial reflector to be reflected and resonated. The radiation detector may be configured to determine the gain or increase in intensity of the output radiation over the known intensity of the input seed radiation, which gain or increase may be attributed to stimulated scattering.

Accordingly, with continued reference to the method 100 of FIG. 1, irradiating a sample at block 110 may include irradiating a sample with an input transverse radiation and an input seed radiation having different frequencies. Likewise, detecting radiation at block 150 may include detecting a gain over the intensity of the seed radiation. The seed radiation frequency may be varied over a set of predetermined frequencies corresponding to different molecules to determine whether the sample within the chamber contains a molecule corresponding to one of these frequencies. For example, the seed radiation may be provided at an inelastically scattering frequency for adenine. If the gain over the seed radiation is sufficiently zero then there was no simulated scattering and it may be concluded that the sample did not contain adenine. Then the frequency of the seed radiation may be adjusted to that corresponding to other nucleotide bases until the gain is sufficiently nonzero indicating that the sample may contain that particular base. If none of the frequencies cause the gain to become sufficiently nonzero, the sample may be removed from the chamber and another sample added thereto.

The concepts of seed and transverse input radiations discussed in FIG. 8 may also be applied to a spectroscopic analysis system similar to the ones shown in FIGS. 5-6. For example, input transverse excitation radiation may be transmitted in through window 620, input seed radiation may be transmitted in through window 660, and scattered radiation may be transmitted out through window 660. Portions of the input transverse radiation that do not irradiate the sample may be removed through a window at location 679.

Accordingly, in embodiments of the invention employing a stimulated Raman analysis, a single molecule of interest may be positioned within a resonant chamber that is capable of optically amplifying the intensity of inelastically scattered stimulated Raman radiation by causing resonance enhanced stimulated scattering events that aid in increasing or amplifying the intensity of the signal to an extent that allows detection and accurate identification of the single molecule of interest. As an example, a single nucleic acid derivative of interest may be positioned in a resonant chamber having two opposing reflectors. The first reflector has a high reflectivity for both an excitation radiation and an inelastically scattered Raman radiation, while the second reflector has a high reflectivity for the excitation radiation and has a sufficient transmittance for the inelastically scattered Raman radiation. In one aspect, a high reflectivity may be greater than approximately 99% (e.g., 99.5%-99.9%) while a sufficient transmittance may be a reflectivity not greater than 99%. The two opposing reflectors are separated by a distance that is sufficient to resonate the inelastically scattered Raman radiation. The distance may be determined based on inelastically scattered Raman radiation for the single nucleic acid derivative, or for a plurality of nucleic acid derivatives so that the chamber may be used for identifying different derivatives.

Accordingly, a sample containing a single molecule of interest may be analyzed with stimulated Raman spectroscopy. In addition to stimulated Raman spectroscopy, another suitable form of coherent Raman spectroscopy is Coherent Anti-Stokes Raman Spectroscopy (CARS), which employs a coherent anti-Stokes Raman scattering phenomenon. Many other forms of Raman, such as spontaneous Raman and surface enhanced Raman spectroscopy (SERS), involve spontaneous emission of random and non-coherent inelastically scattered radiation. In contrast, CARS inherently produces a highly directional and coherent output inelastically scattered radiation signal. Rather than due to resonance, as in stimulated Raman, the coherency is provided by coherent build up of amplitudes for phase matched radiations. As used herein, CARS will encompass various implementations of CARS, such as time-resolved CARS, scanned CARS, OPO CARS, MAD CARS, PARS, and others. The CARS radiation signal is sufficiently coherent and intense to allow detection of even a single molecule of interest. The spectral shape and intensity of the CARS output signal contains the spectral characteristics of the sample and may be used to identify the sample. Accordingly, the present inventors contemplate employing CARS to analyze and identify a single nucleic acid derivative in conjunction with nucleic acid sequencing.

CARS is a four-wave mixing spectroscopy. During CARS a sample in a chamber is irradiated and excited with a first radiation having a first wavelength ($w_1$) and often a second radiation having a second wavelength ($w_2$) that overlap and are phase matched (i.e., they spatially and temporally overlap) in order to induce the sample to irradiate coherent anti-Stokes scattered radiation having a third wavelength ($w_3$) that is related to the first and second frequencies according to the relationship, $w_3=2w_1-w_2$.

Figure 9:
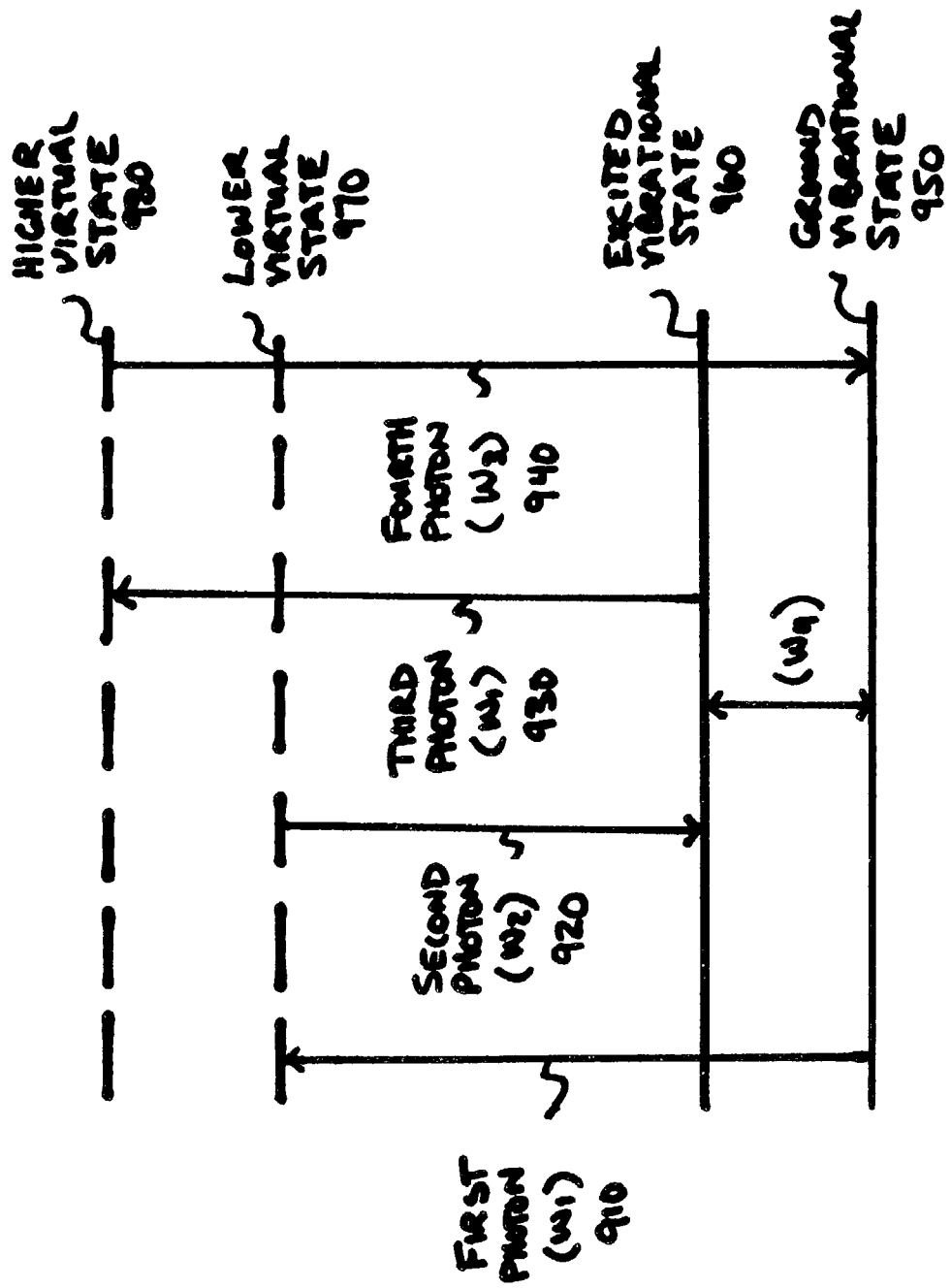
FIG. 9 shows an energy level diagram for a coherent anti-Stokes Raman Spectroscopy process used to analyze a sample, according to embodiments of the invention.

FIG. 9 shows an energy diagram for a CARS process used to analyze a molecule of a sample, according to embodiments of the invention. Energy of the molecule is plotted on the y-axis and the progression of the CARS process is plotted on the x-axis. For convenience, the discussion will refer to a photon, although often in practice a radiation containing at least one but often many photons will be used to analyze the sample. Initially, the molecule is excited coherently with a first photon at wavelength ($w_1$) 910 in order to induce an emission of a second photon at wavelength ($w_2$) 920. The first photon is often provided as a laser beam pulse directed at the chamber to irradiate the molecule. As shown, the first photon excites the molecule from a ground vibrational state 950 to a lower virtual state 970. The emitted second photon brings the molecule from the virtual state 870 down to a lower excited vibrational state 960. The excited vibrational state differs from the ground vibrational state by vibratory transition of Raman shift ($w_4$). The molecule may emit the second photon by either spontaneous or stimulated emission however coherent stimulated emission is used in CARS. Often, the molecule will be exposed by another photon also of wavelength ($w_2$) in order to induce stimulated emission of the second photon. Stimulated emission is relatively more probable than spontaneous emission and may lead to higher CARS signal intensities that facilitate detection and molecule identification. The stimulated emission is often induced by irradiating the chamber with a second radiation having the second wavelength ($w_2$), concurrently with the irradiation with the first radiation (the first photon).

The molecule in the lower excited vibrational state 960 is subsequently irradiated with a third photon at wavelength ($w_1$) 930. Irradiation with a laser beam pulse may also provide this photon. The third photon excites the molecule from the excited vibrational state 960 to a higher virtual state 980. The molecular vibrations oscillate in phase and interfere constructively. The molecule emits a fourth photon at wavelength ($w_3$) to drop from the higher virtual state to the ground vibrational state. The wavelength of the fourth photon is twice the wavelength of the first and third photons minus the wavelength of the emitted second photon (i.e., $w_3=2w_1-w_2$). In essence, CARS disproportionates or divides two ($w_1$) photons into a ($w_2$) photon and a ($w_3$) photon. A phase matching condition determines the direction of the coherent CARS signal. As will be discussed further below, the present inventors contemplate employing various geometric configurations of beams to take advantage of this property to help spatially isolate the coherent CARS signal from input excitation beams, in order to facilitate detection and identification of molecules. The intensity of the emitted CARS signal is directly related to the intensity of the excitation radiations.

Different ways of exposing the sample to these photons are known in the arts. In one approach, the sample may be concurrently irradiated with a first laser beam pulse of the wavelength $w_1$, a second laser beam pulse of the wavelength $w_2$, and a third laser beam pulse of the wavelength ($w_1$). In practice, the first laser beam pulse can also serve as a third laser beam pulse as they have the same wavelength, ($w_1$). Electronics to provide concurrent laser beam pulses from multiple lasers are commercially available. Such synchronization electronics include SynchroLock from Coherent (Santa Clara, Cailf.) or Lok-to-Clok from Spectra-Physics (Mountain View, Cailf.). Alternatively, in another approach the sample may be continually irradiated with a laser beam of the wavelength ($w_1$) and intermittently irradiated with a pulse or scan of a laser beam of the wavelength ($w_2$). When the difference ($w_1$-$w_2$) substantially coincides or matches the wavelength of a molecular vibration of the sample, for example the vibratory transition ($w_4$), the intensity of the CARS signal is often significantly enhanced. A spectrum may be generated for a range of the wavelength ($w_2$) or the difference ($w_1$-$w_2$). Often, ($w_2$) is continually changed, varied, or scanned, while holding ($w_1$) fixed, and simultaneously recording the corresponding CARS signals. Alternatively, ($w_1$) is continually changed, varied, or scanned, while holding ($w_2$) fixed, and simulateneously recording the corresponding CARS signals. In another embodiment, both ($w_1$) and ($w_2$) are continually changed, varied, or scanned, to obtain the desired ($w_1$-$w_2$), while recording the corresponding CARS signals. In one approach a tunable broadband dye laser is scanned over the desired range of wavelength. Another approach involves using a broadband Stokes laser covering the whole range of frequencies concurrently. Alternatively, signal and idler beams from optical parametric oscillator can be used to scan ($w_1$-$w_2$).

In order for a CARS process to occur efficiently energy and momentum conservation need to occur. During CARS the output signal is built by coherent addition of amplitudes. In the CARS four-wave mixing process, it will often be desirable to impose a phase matching condition on the wave vectors of the input excitation radiations and output coherent anti-Stokes radiation in order to achieve good intensities of the output coherent radiation. The amplitudes should be substantially in phase, that is the beams aligned to provide phase matching between the sum of two incoming waves at wavelength ($w_1$) and the sum of output waves at wavelength ($w_2$) and ($w_3$). When the phase matching condition is satisfied, the strength or intensity of the output anti-Stokes wave should be near maximum. This results in the sample irradiating or emitting a coherent resonance enhanced anti-Stokes scattered radiation, often as a coherent, collimated, highly-directional beam with a predetermined direction, rather than as a weak and randomly scattered signal as would be expected in spontaneous Raman spectroscopy. The predetermined direction of the CARS signal may allow various configurations that allow it to be geometrically or configurationally separated from the excitation radiation.

Figure 12:
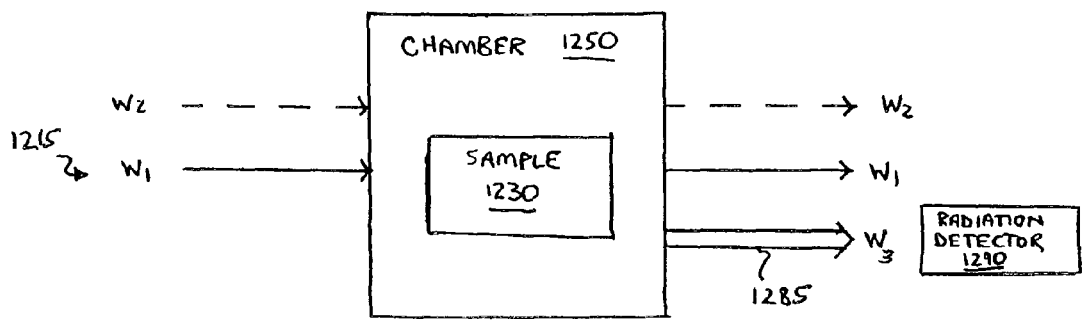
FIG. 12 shows a forward-scattered configuration for implementing coherent anti-Stokes Raman spectroscopy, according to embodiments of the invention.
Figure 13:
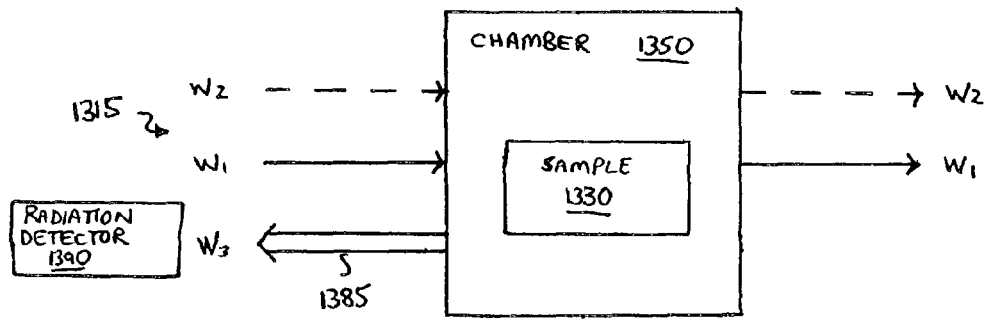
FIG. 13 shows a back-scattered configuration for implementing coherent anti-Stokes Raman spectroscopy, according to embodiments of the invention.
Figure 11:
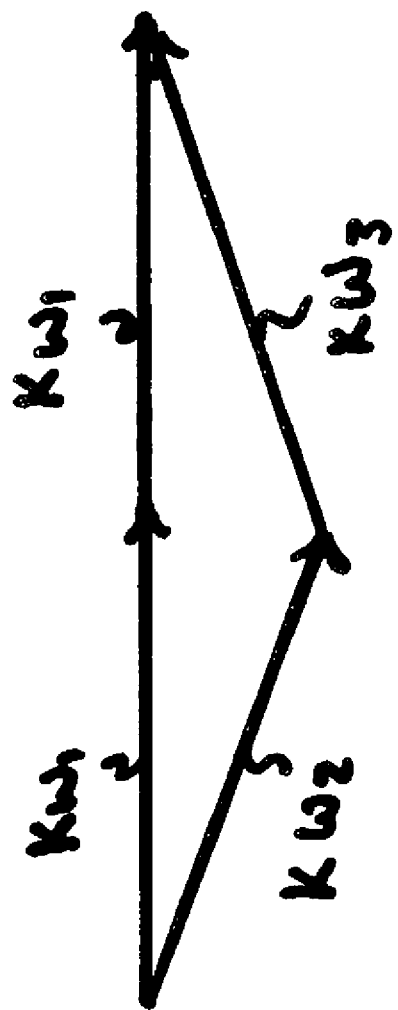
FIG. 11 shows momentum conservation for a cross-beam configuration similar to that shown in FIG. 10, according to embodiments of the invention.

A number of prior art phase matching beam configurations or geometries are known in the arts including a collinear CARS geometry, a BOX CARS geometry, a Folded BOX CARS geometry, and a USED CARS geometry. Any of these may potentially be used. Additionally, the inventors contemplate using configurations that help separate or isolate the CARS radiation signal from input excitation radiation. FIGS. 11-13 show exemplary configurations of excitation radiation beams that when phase matched may help to spatially separate and isolate the CARS signal from the excitation beams at the radiation detection end, according to various embodiments of the invention. Advantageously, in these exemplary configurations, the CARS signal beam is spatially separated and isolated from the excitation beams at the radiation detection end, which may facilitate sample identification. Other configurations will be apparent to those having an ordinary level of skill in the art and the benefit of the present teachings.

Figure 10:
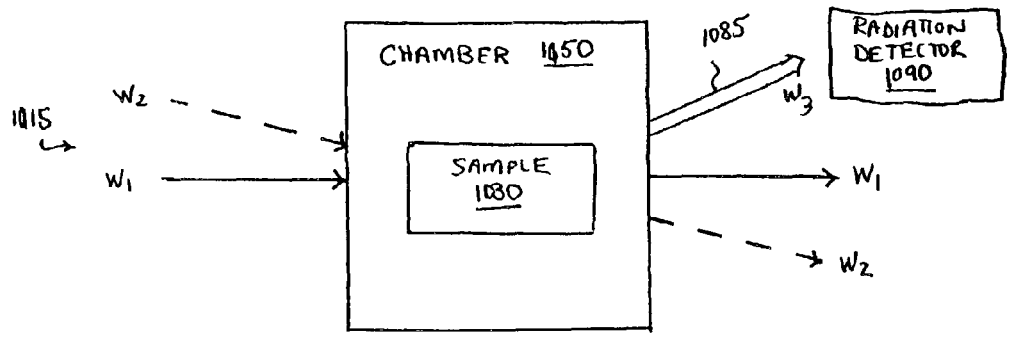
FIG. 10 shows a cross-beam configuration for implementing coherent anti-Stokes Raman spectroscopy, according to embodiments of the invention.

FIG. 10 shows a cross-beam configuration, according to embodiments of the invention. In the cross-beam configuration, an input first ($w_1$) and second radiation ($w_2$) are provided to a chamber 1050 with an angle relative to one another so that they irradiate a sample 1030 within the chamber and subsequently separate from one anther and from a coherent anti-stokes scattered radiation ($w_3$) that is irradiated from the sample. In this way, the configuration helps separate the input radiation from the output coherent scattered radiation, and wavelength selection or filtering may be avoided. The chamber may be similar to other chambers disclosed herein. The chamber may, but need not, be a resonant chamber and may, but need not, contain reflectors or have a size or shape to facilitate resonance.

FIG. 11 shows momentum conservation for a cross-beam configuration similar to that shown in FIG. 10. The phase matching condition determines the direction of the coherent anti-Stokes radiation. Because of the conservation of energy and momentum in a four-wave mixing process, a phase matching condition is imposed on the wave vectors of the input and anti-Stokes output waves. When the phase matching condition is sufficiently satisfied the output strength is near maximum and the direction and momentum of the coherent anti-Stokes photons are related to the direction and momentum of the excitation photons. This is shown graphically in FIG. 11 wherein two vectors for the first excitation wavelength ($2k_{w1}$) and one vector for the second excitation wavelength ($k_{w2}$) are combined to give a vector for the coherent anti-Stokes radiation ($k_{w3}$), or mathematically $k_{w3}=2 k_{w1}-k_{w2}$. The length of the vectors represents the photons momentum. The configuration of the direction of the excitation radiations allows the CARS signal photon to be geometrically separated from the input excitation photons. This may facilitate detection of the emitted CARS photon.

FIG. 12 shows a forward-scattered configuration, according to embodiments of the invention. In this configuration, the coherent radiation is not separated from the input radiations, and a wavelength selection device, such as a filter, may be used to isolate the coherent radiation.

FIG. 13 shows a back-scattered configuration, according to embodiments of the invention. In this configuration, as in the cross-beam configuration, the coherent radiation is separated from the input radiations. The intensity of the coherent radiation in this configuration is often comparable with that of the forward-scattered configuration when the sample size is less than the excitation wavelength, although in other instances it may be desirable to use a forwardscattered configuration and appropriate wavelength selection device to obtain a stronger signal.

Figure 14:
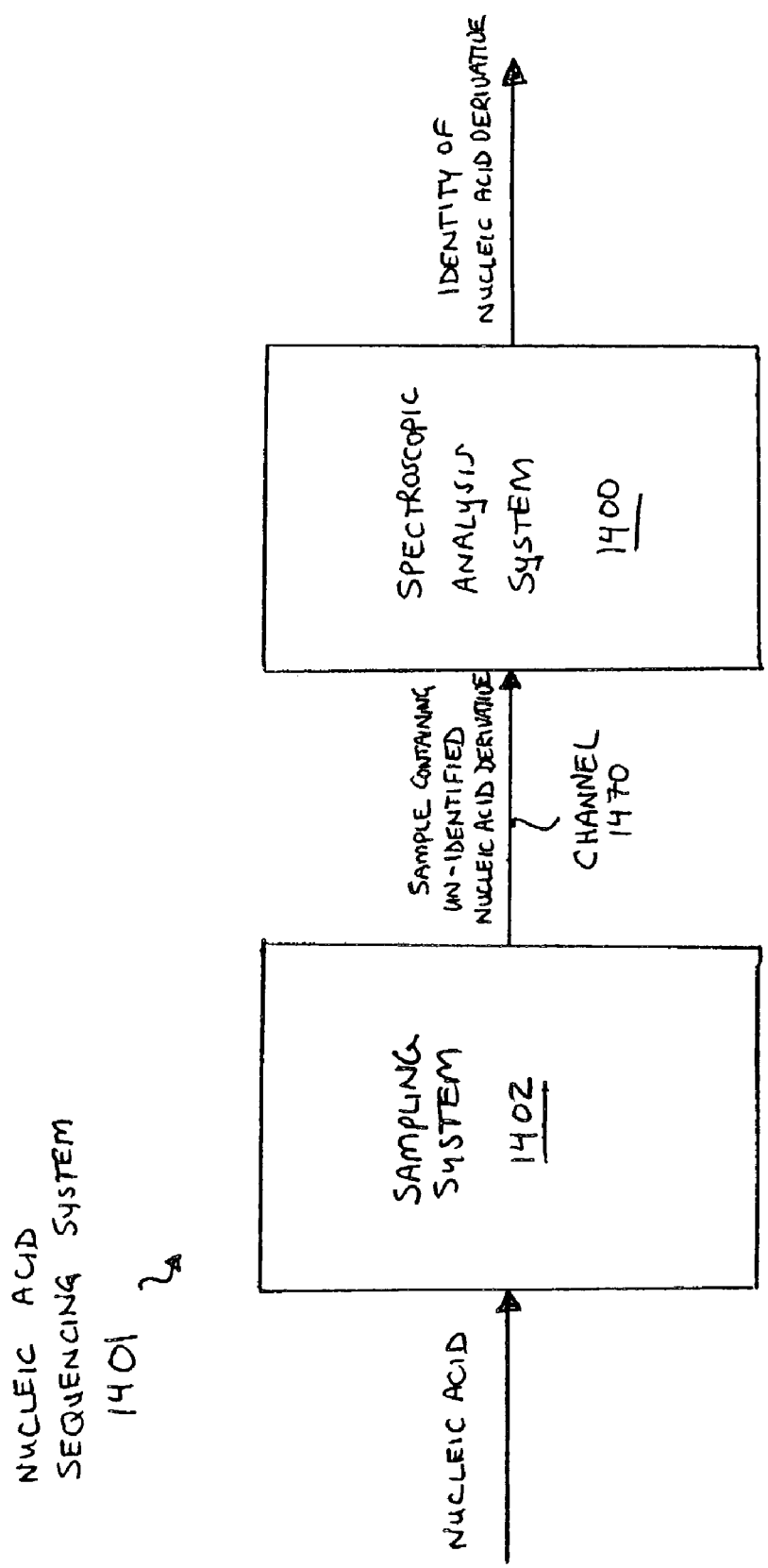
FIG. 14 shows a nucleic acid sequencing system in which embodiments of the invention may be implemented.

FIG. 14 shows a nucleic acid sequencing system 1401 in which embodiments of the invention may be implemented. A nucleic acid may be provided to a sampling system 1402. The sampling system may include enzymes or other cleavers of nucleic acids to remove or derive a single nucleic acid derivative from the nucleic acid. In one instance, the system may include an exonuclease enzyme that breaks down a nucleic acid chain by removing single nucleotides one by one from the end of a chain. The sampling system may also include equipment to prepare the sample, for example to dilute the nucleic acid derivative in an aqueous solution and supply any additives. The sample may be added to the spectroscopic analysis system 1400, for example though a fluid channel 1470. The analysis system performs a Raman spectroscopic analysis of the sample, as described elsewhere herein, in order to identify the nucleic acid derivative. For example, the analysis system may determine whether the sample contains a single base selected from the group comprising adenine, cytosine, guanine, thymine, and uracil. The identity of the nucleic acid derivative may be stored in a memory as part of an ordered sequence for the input nucleic acid, analyzed as part of the sequence to solve a medical problem, for example to diagnose or treat a disease, or used for other purposes.

Thus, spectroscopic analysis chambers and methods for analyzing samples within those chambers are disclosed. While the invention has been described in terms of several embodiments, those skilled in the art will recognize that the invention is not limited to the embodiments described, but may be practiced with modification and alteration within the spirit and scope of the claims. It is to be realized that the optimum dimensional relationships for the parts of the invention, to include variations in size, materials, shape, form, function and manner of operation, assembly and use, are deemed readily apparent to one of ordinary skill in the art, and all equivalent relationships to those illustrated in the drawings and described in the specification are intended to be encompassed by the present invention. The description is thus to be regarded as illustrative instead of limiting.

What is claimed is:

1. A method for determining the identity of a plurality of molecules of interest in a sample comprising:
    determining a Stokes Raman shift for at least two known molecules of interest;
    exciting the sample in a resonance chamber, which chamber comprises a reflector and a partial reflector, with at least two light sources, wherein a predetermined distance between reflectors is a function of wave length corresponding to prominent peaks in the Raman spectra for the two known molecules of interest, thereby selectively inelastically scattering radiation from the sample;
    resonating the inelastically scattered radiation between the reflector and partial reflector to amplify the intensity of the inelastically scattered radiation;
    transmitting the amplified inelastically scattered radiation from the chamber;
    detecting the transmitted amplified inelastically scattered radiation; and
    determining whether the detected transmitted amplified inelastically scattered radiation corresponds to one of the two known molecules of interest.

2. The method of claim 1, wherein the at least two light sources irradiate in two directions, comprising a seed radiation in a first direction and a transverse radiation in a second direction, the first direction being perpendicular to the second direction.

3. The method of claim 2, wherein the seed radiation and transverse radiation are different frequencies.

4. The method of claim 2, wherein detecting the separate transmitted amplified inelastically scattered radiation includes detecting a gain over the intensity of the seed radiation.

5. The method of claim 1, wherein the reflectors are opposite and parallel to one another within the resonance chamber and centered along a common optical axis.

6. The method of claim 1, wherein the predetermined distance provides a nondestructive relationship between the phases of incident and reflected radiation.

7. The method of claim 1, wherein the reflectors are multi-layer dielectric mirrors.

8. The method of claim 7, wherein the multi-layer dielectric minors contain a layer having a thickness that is based on wavelengths of the separate inelastically scattered radiation for the at least two molecules of interest.

9. The method of claim 1, wherein the reflectors include a partial reflector having sufficient reflectivity to achieve resonance and a sufficient transmittance for the separate amplified inelastically scattered radiation.

10. The method of claim 1, transmitting the separate scattered radiation comprises transmitting the separate amplified inelastically scattered radiation through an outlet window in the partial reflector.

11. The method of claim 1, wherein the resonance chamber includes at least one window to transmit radiation into the chamber and to transmit the separate amplified inelastically scattered radiation out of the chamber.

* * * * *